United States Patent [19]

Bertoncini

[11] Patent Number: 4,879,431
[45] Date of Patent: Nov. 7, 1989

[54] TUBELESS CELL HARVESTER

[75] Inventor: Joseph Bertoncini, Gaithersburg, Md.

[73] Assignee: Biomedical Research and Development Laboratories, Inc., Gaithersburg, Md.

[21] Appl. No.: 323,607

[22] Filed: Mar. 9, 1989

[51] Int. Cl.$^4$ .............................................. C12M 1/12
[52] U.S. Cl. .................................... 435/311; 435/287; 15/302; 15/304; 141/59; 141/244
[58] Field of Search ................ 435/300, 311, 287; 15/302, 304, 321, 322; 141/89, 59, 240, 244

[56] References Cited

U.S. PATENT DOCUMENTS

| | | | |
|---|---|---|---|
| 3,949,771 | 4/1976 | Dodge et al. | 15/321 |
| 4,055,202 | 10/1977 | Greene | 141/59 |
| 4,245,042 | 1/1981 | Weinstein et al. | 435/311 |
| 4,493,896 | 1/1985 | LaMotte et al. | 435/287 |
| 4,635,665 | 1/1987 | Namba et al. | 15/302 |

*Primary Examiner*—Carroll B. Dority
*Attorney, Agent, or Firm*—Breneman & Georges

[57] ABSTRACT

A multi-layered cell harvester having a multi-layered top section and multi-layered bottom section with holes and channels formed in the multiple layers along with vacuum and wash manifolds is provided for removing, filtering and washing the contents from test tubes in a standard test tube rack. The novel multi-layered cell harvester precisely controls an equal volume of wash fluid or reagent to the test tubes and each of the filter areas on a sheet of filter paper areas on a sheet of filter paper by utilizing a wash fluid or reagent reservoir having a purge means and wash channels of equal length formed in the multi layers from the reservoir to the tip of each wash needle where the diameter of each wash channel is the same, or by increasing the diameter of some of the wash channels or a combination thereof. The multi-layered cell harvester can include provisions for separately handling radioactive materials and saving the mother liquid and wash fluids or reagents.

31 Claims, 33 Drawing Sheets

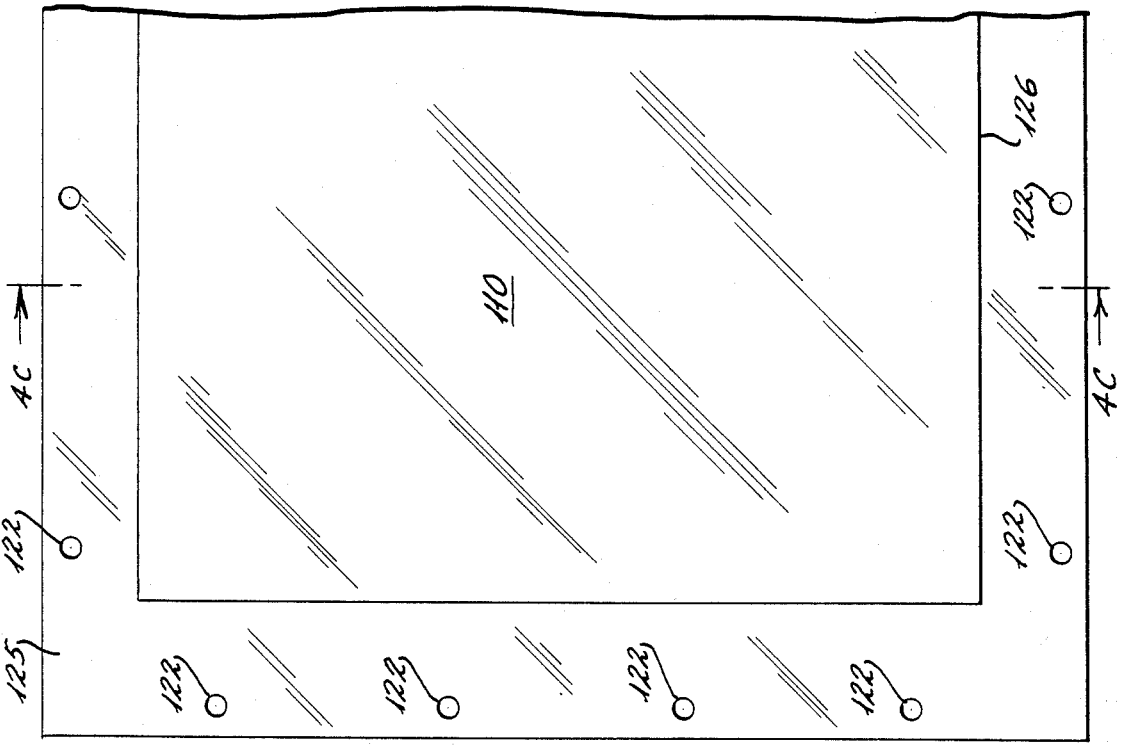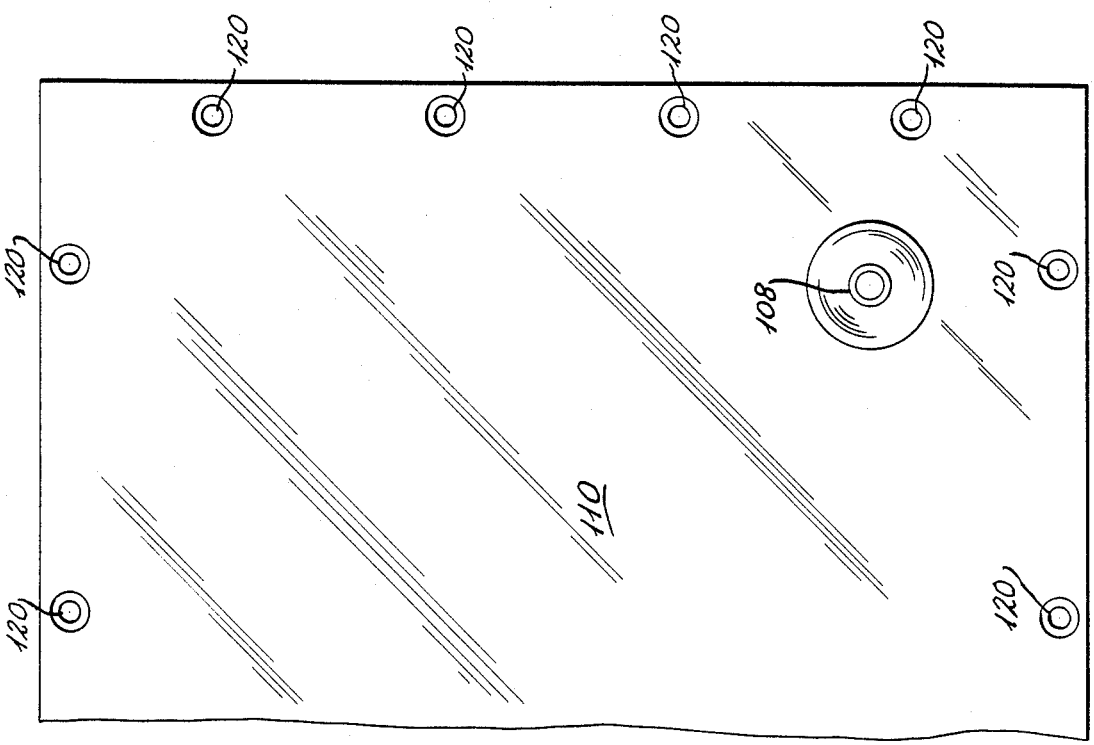

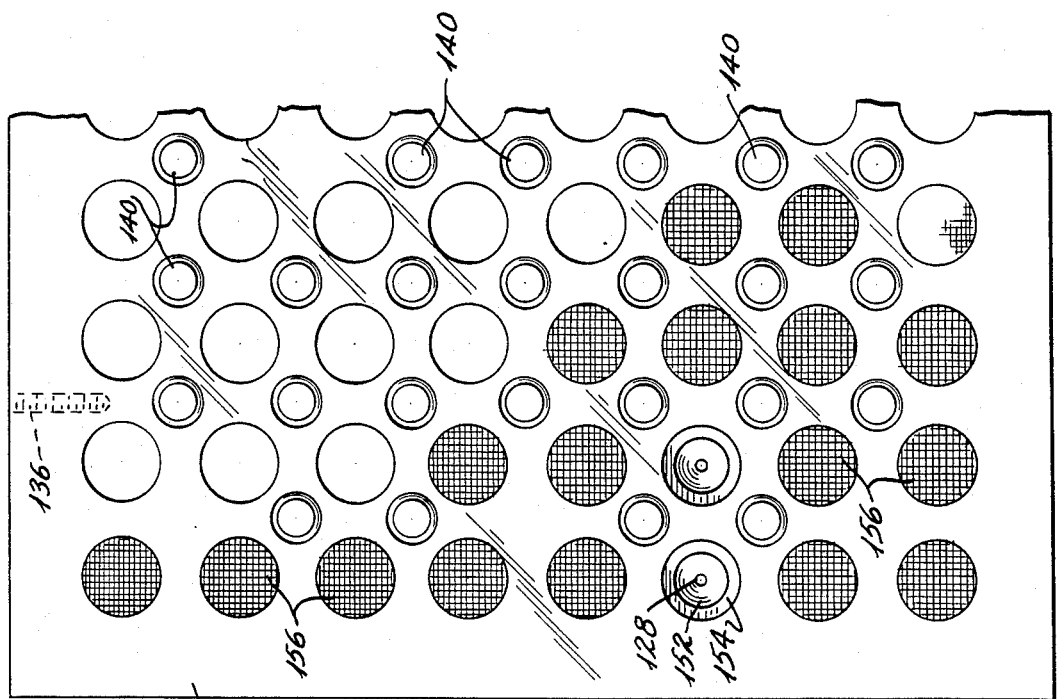
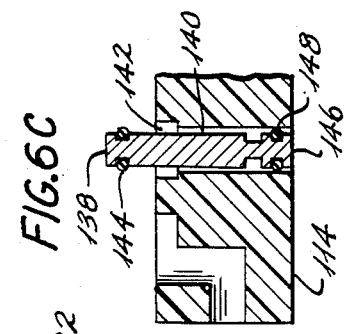
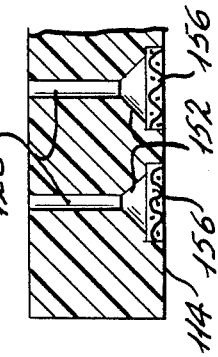
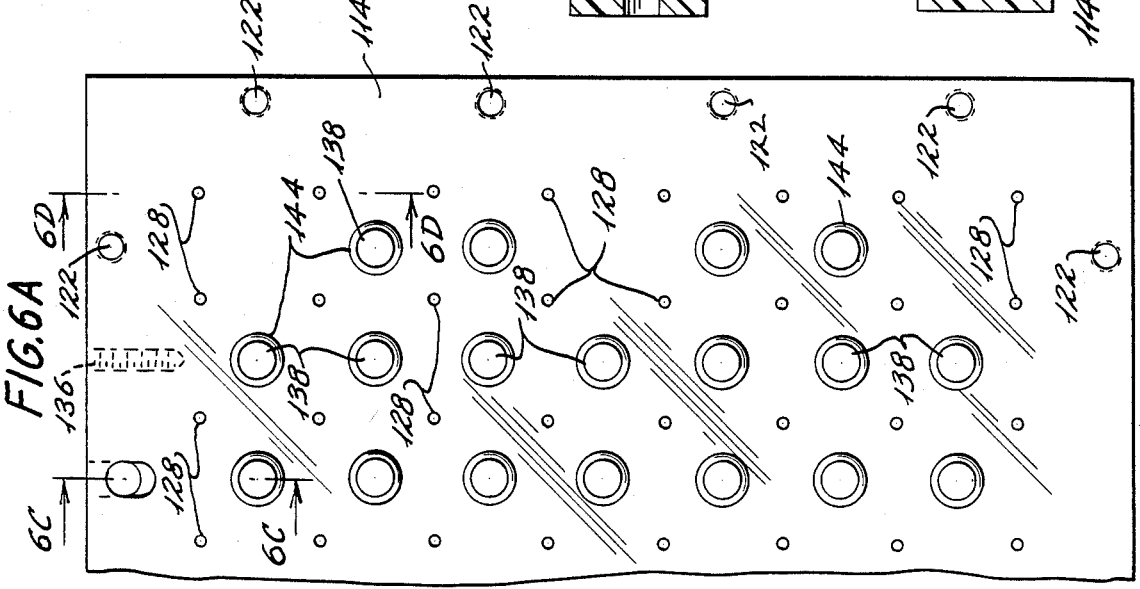

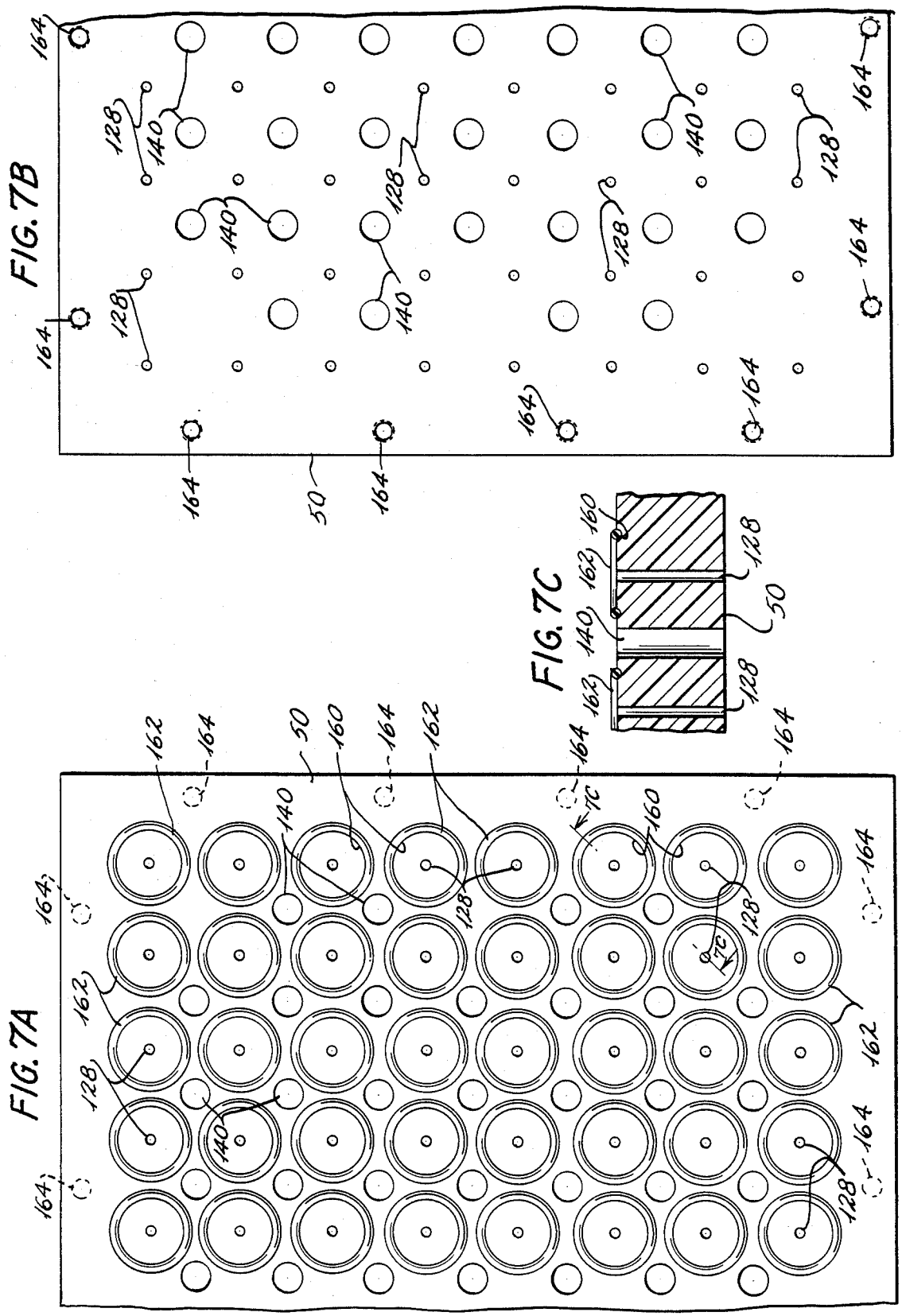

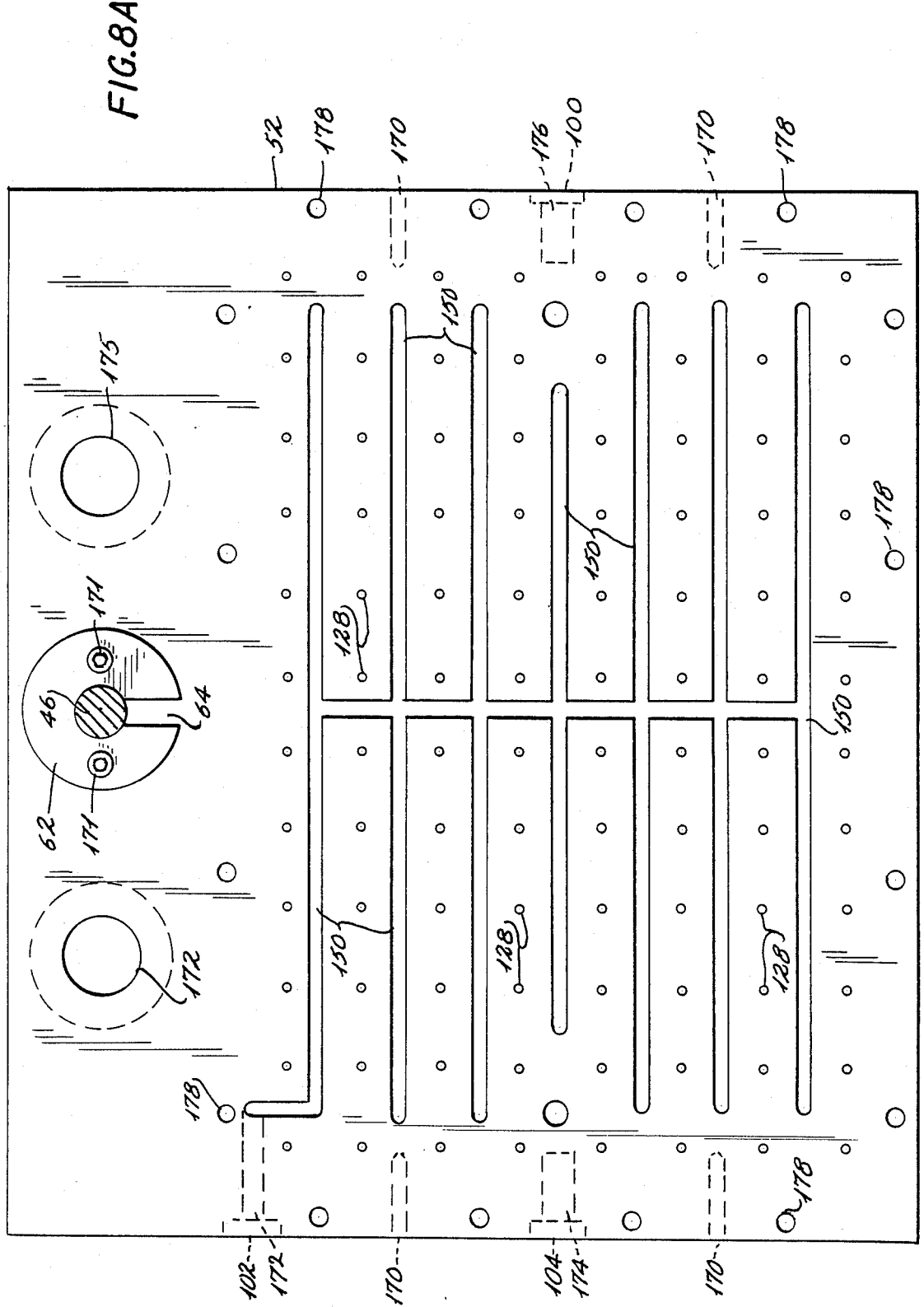

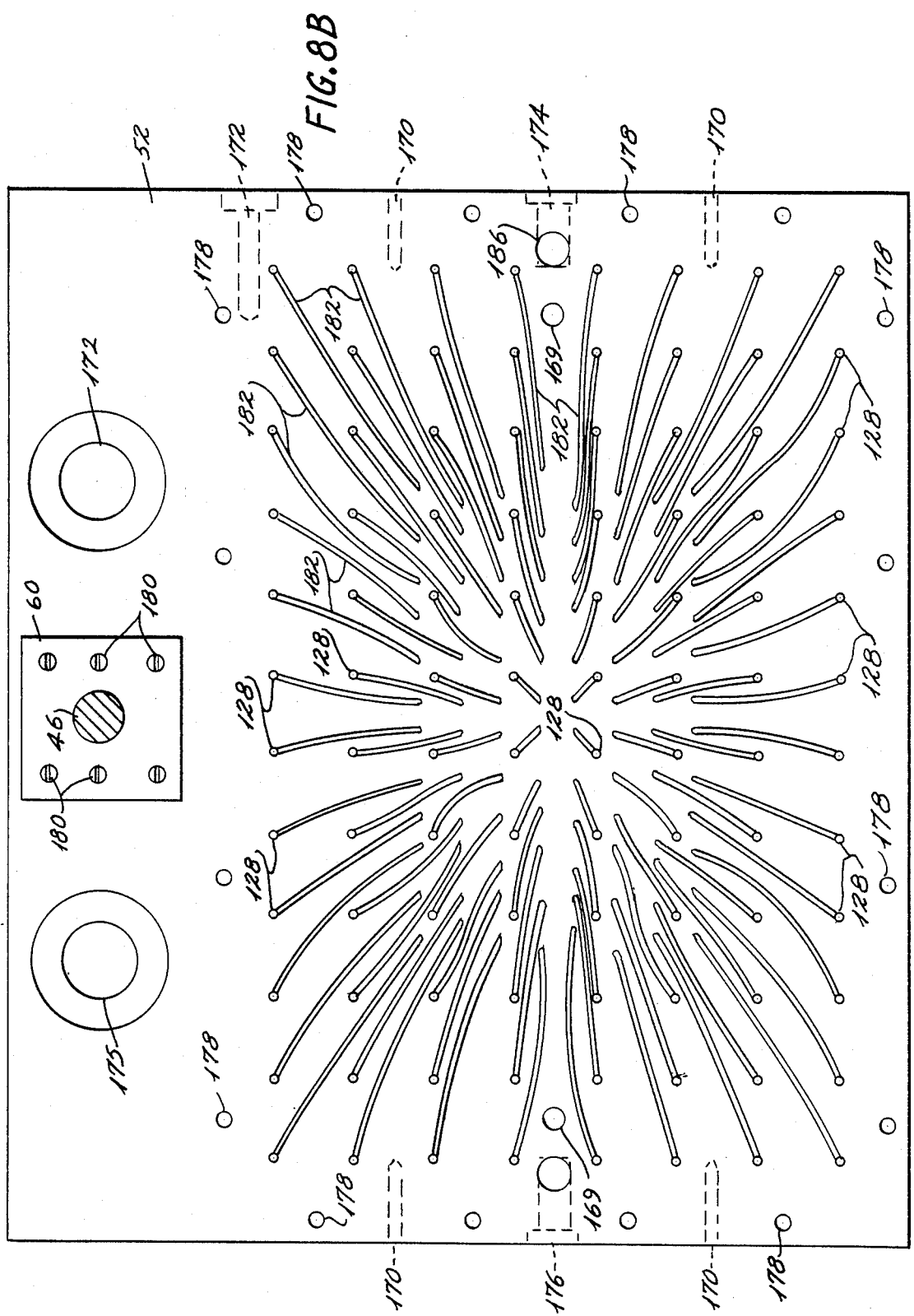

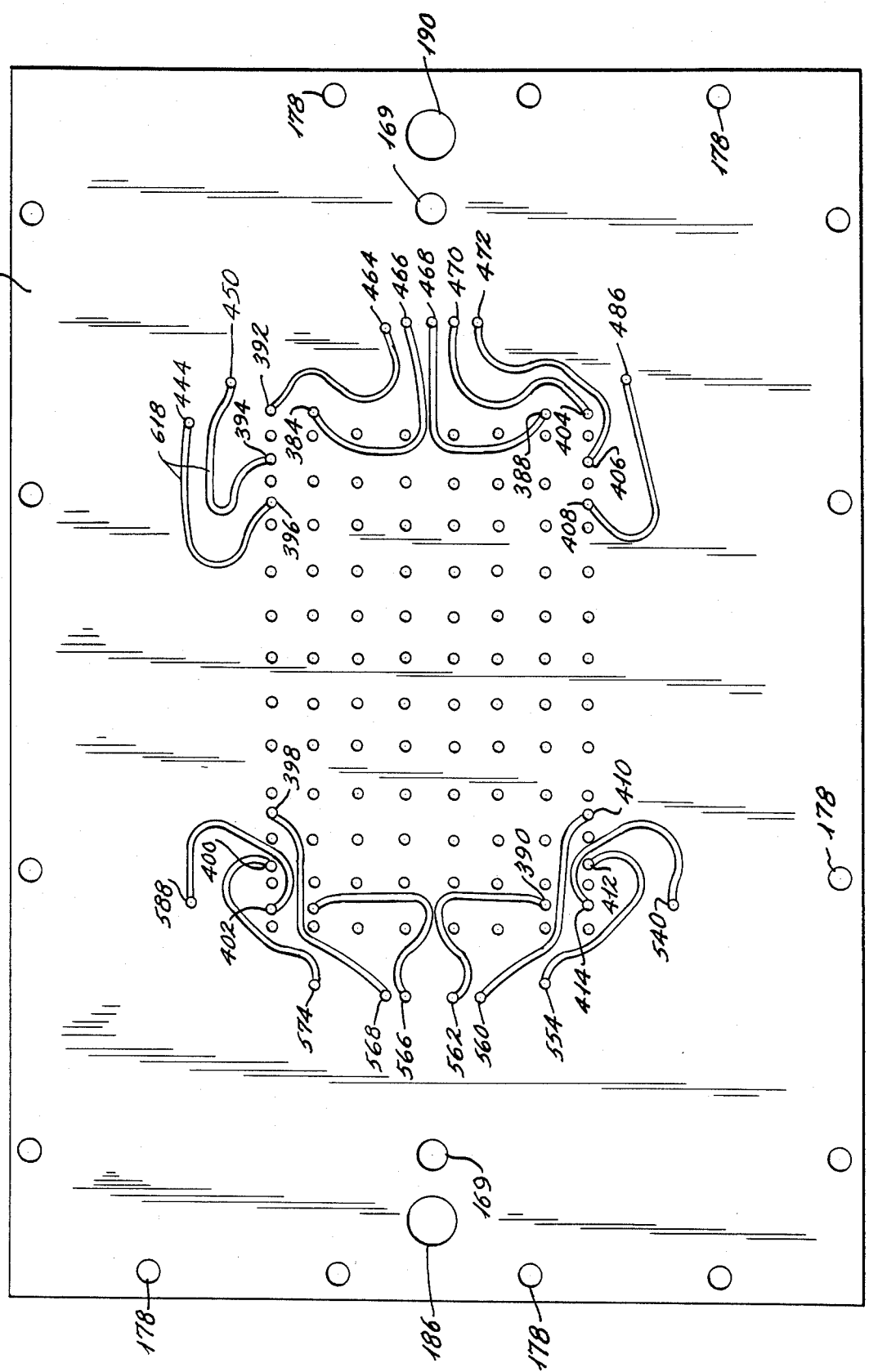

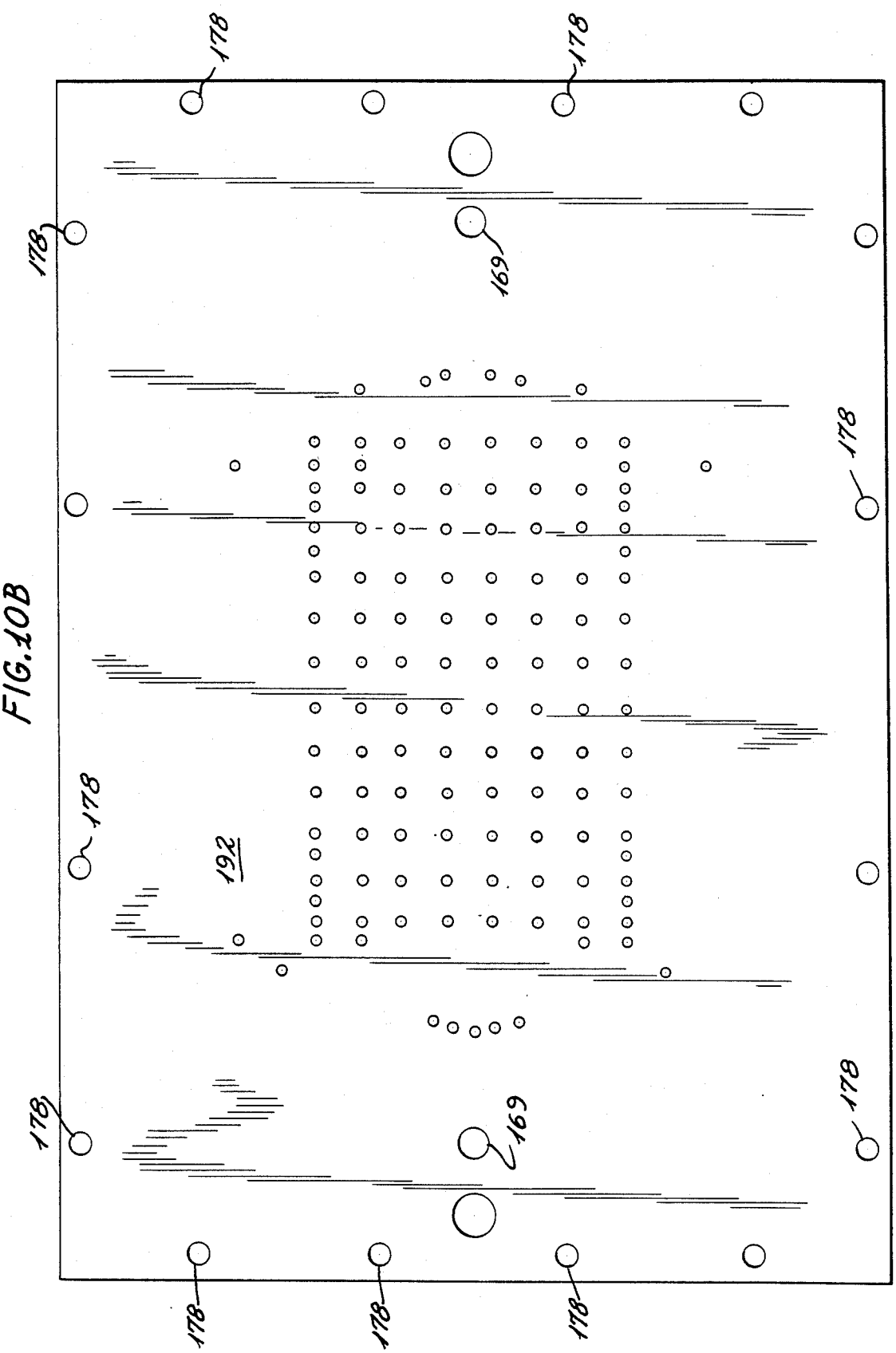

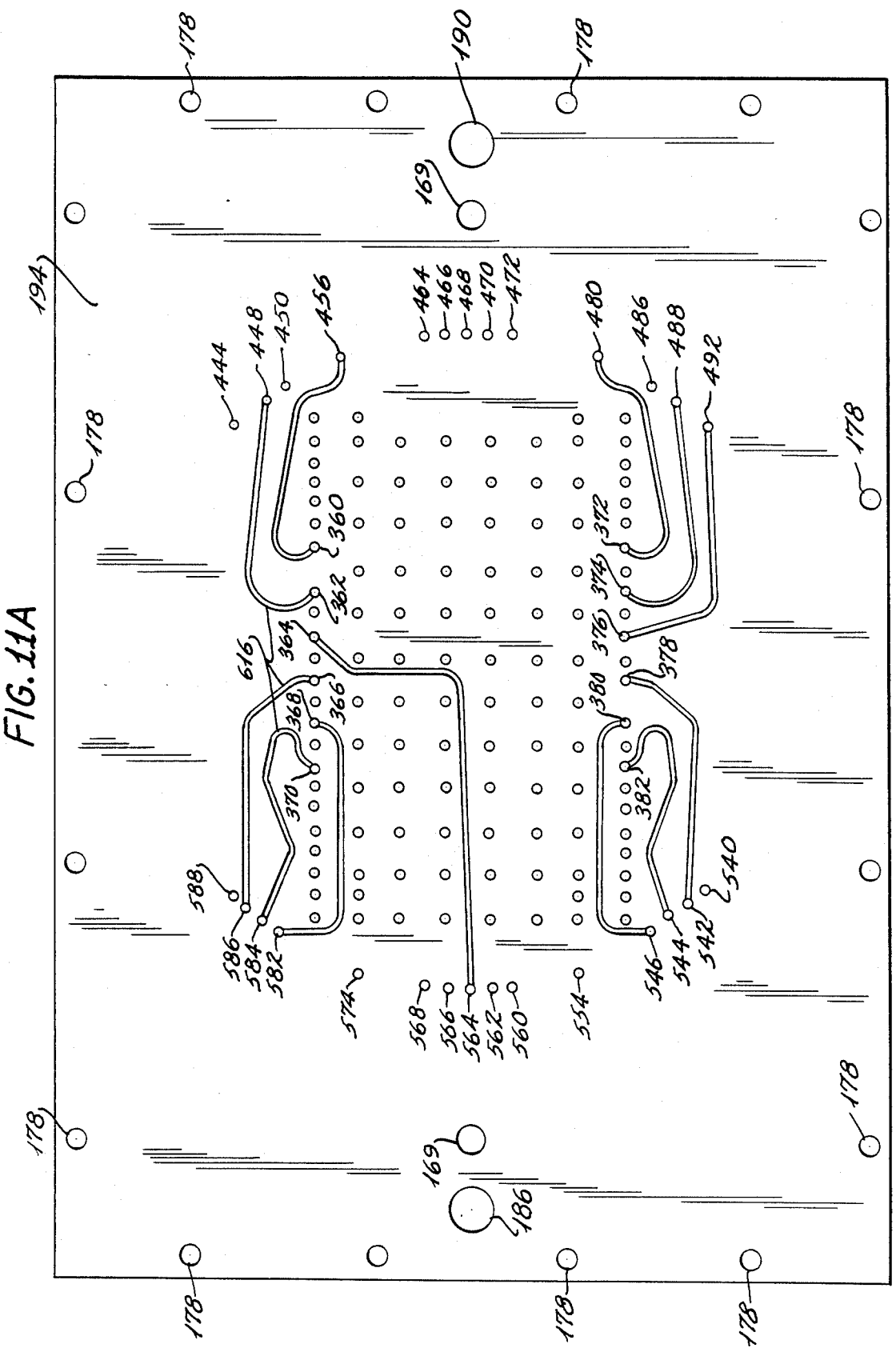

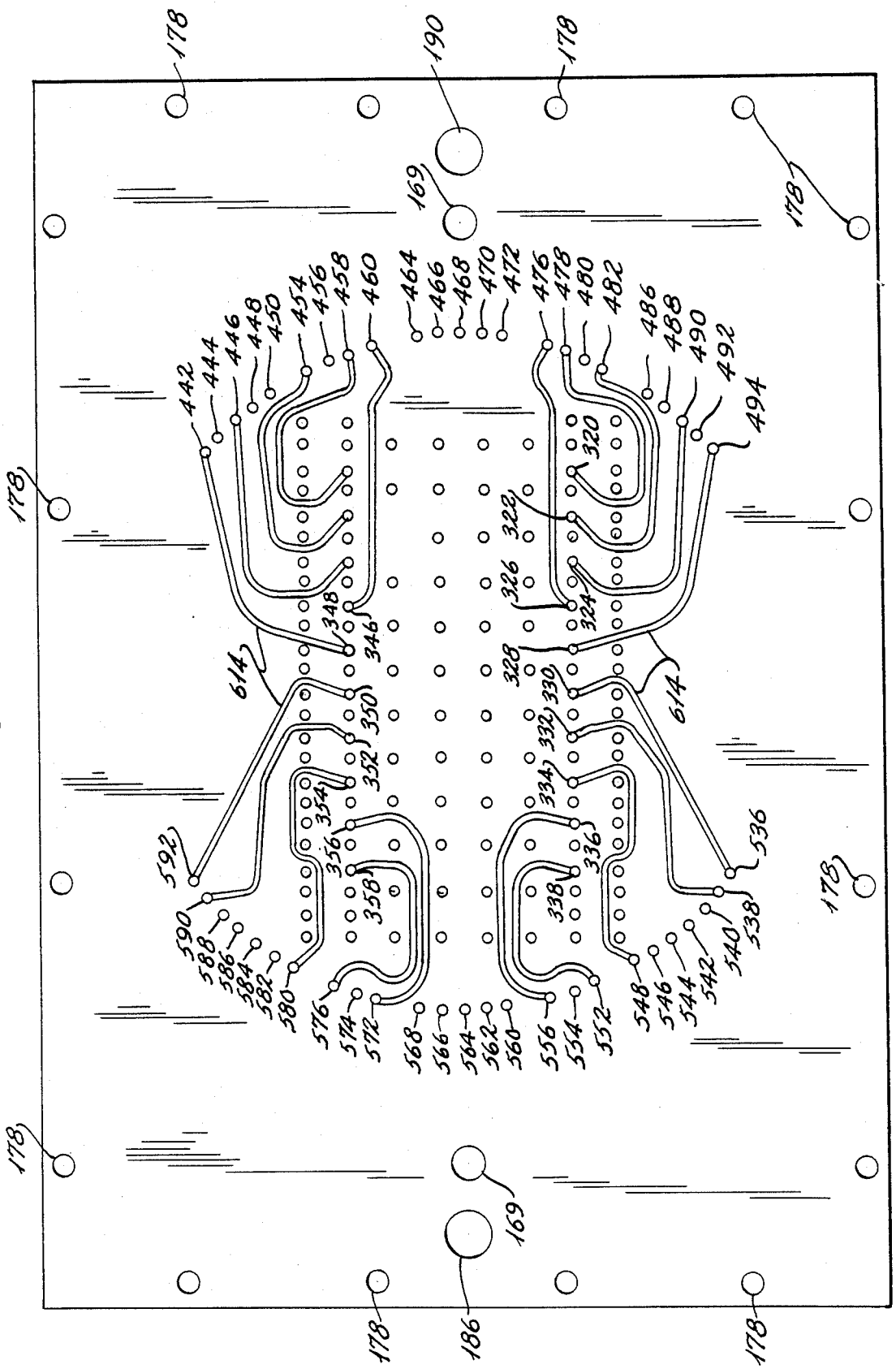

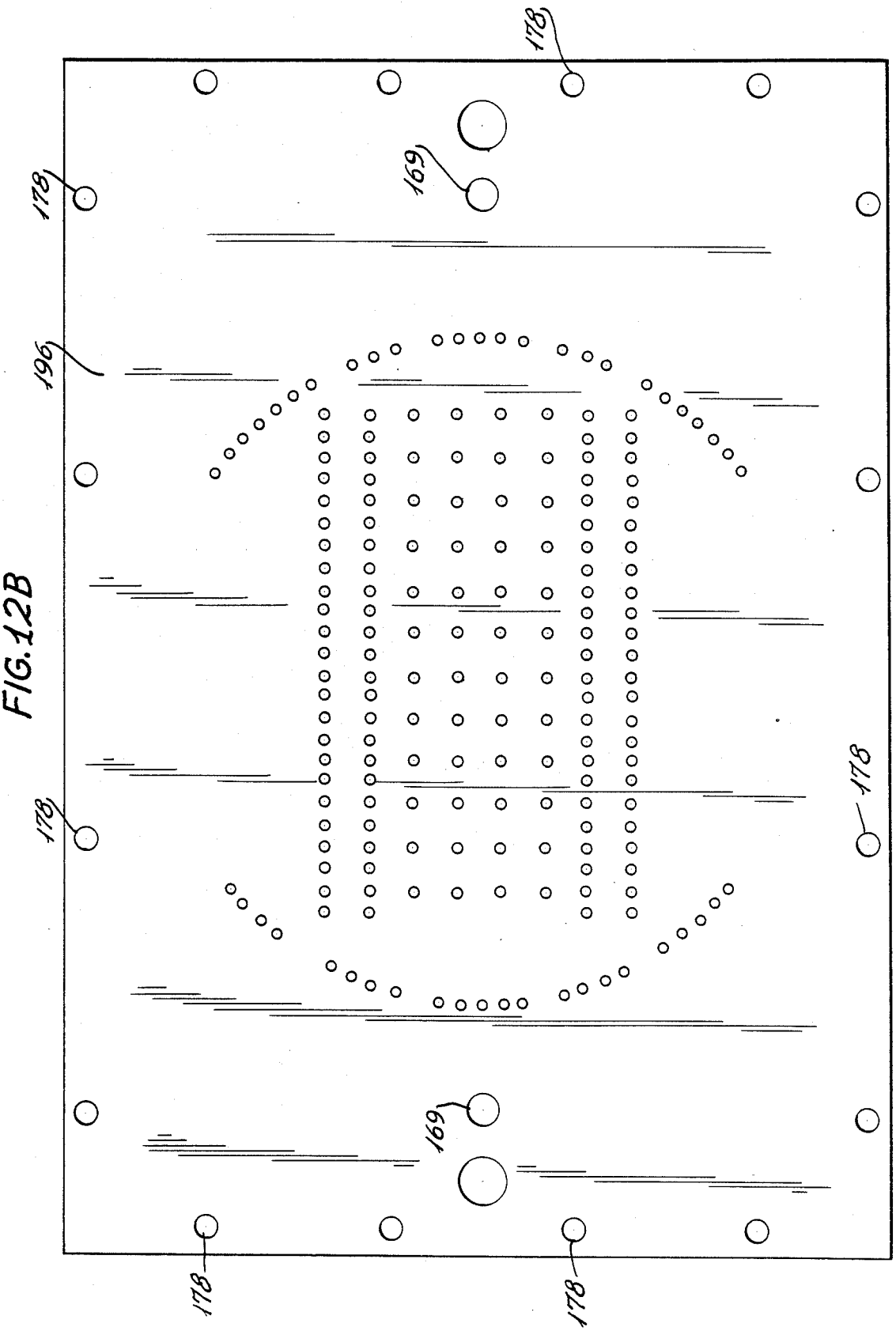

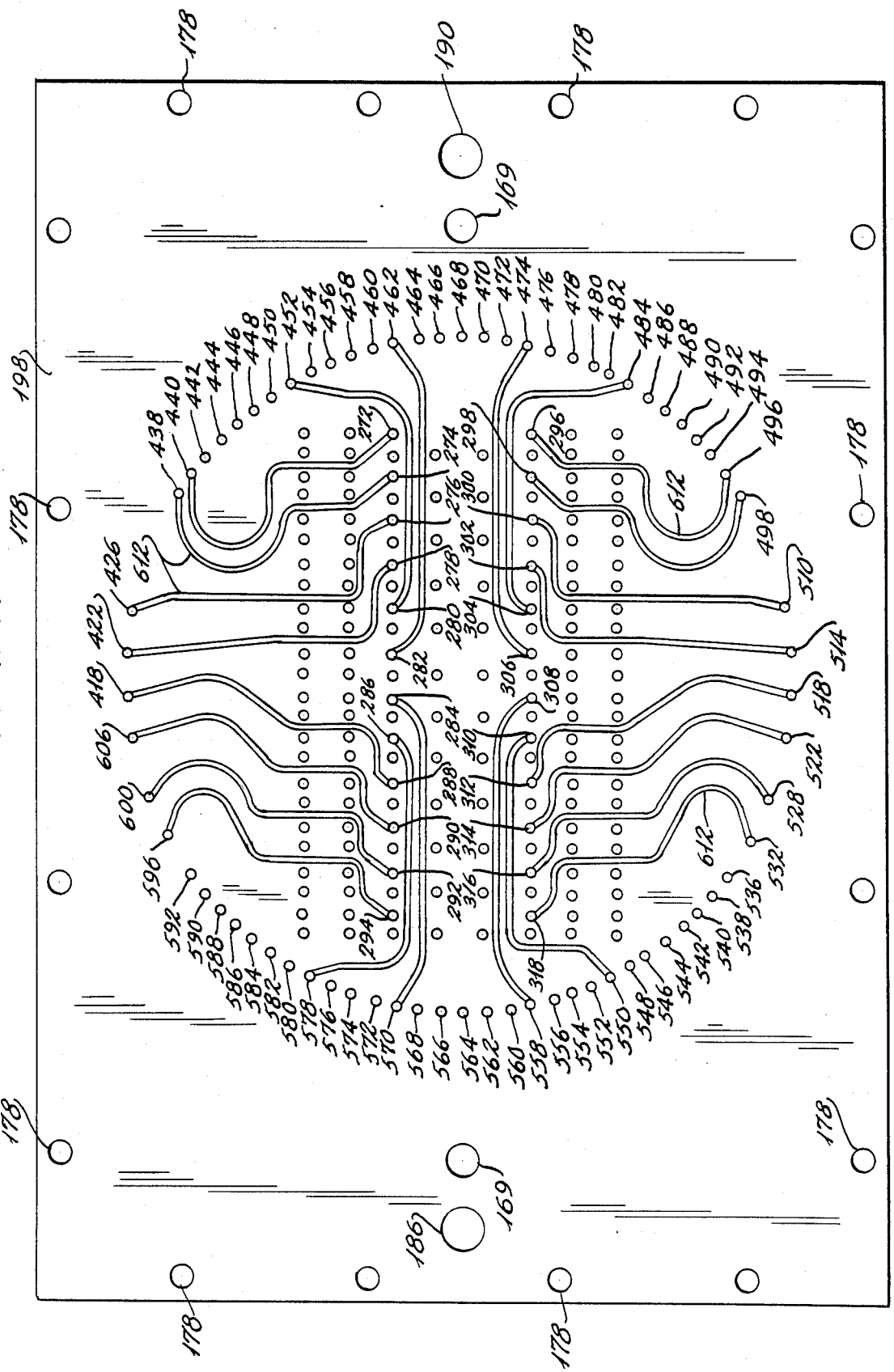

FIG.14B

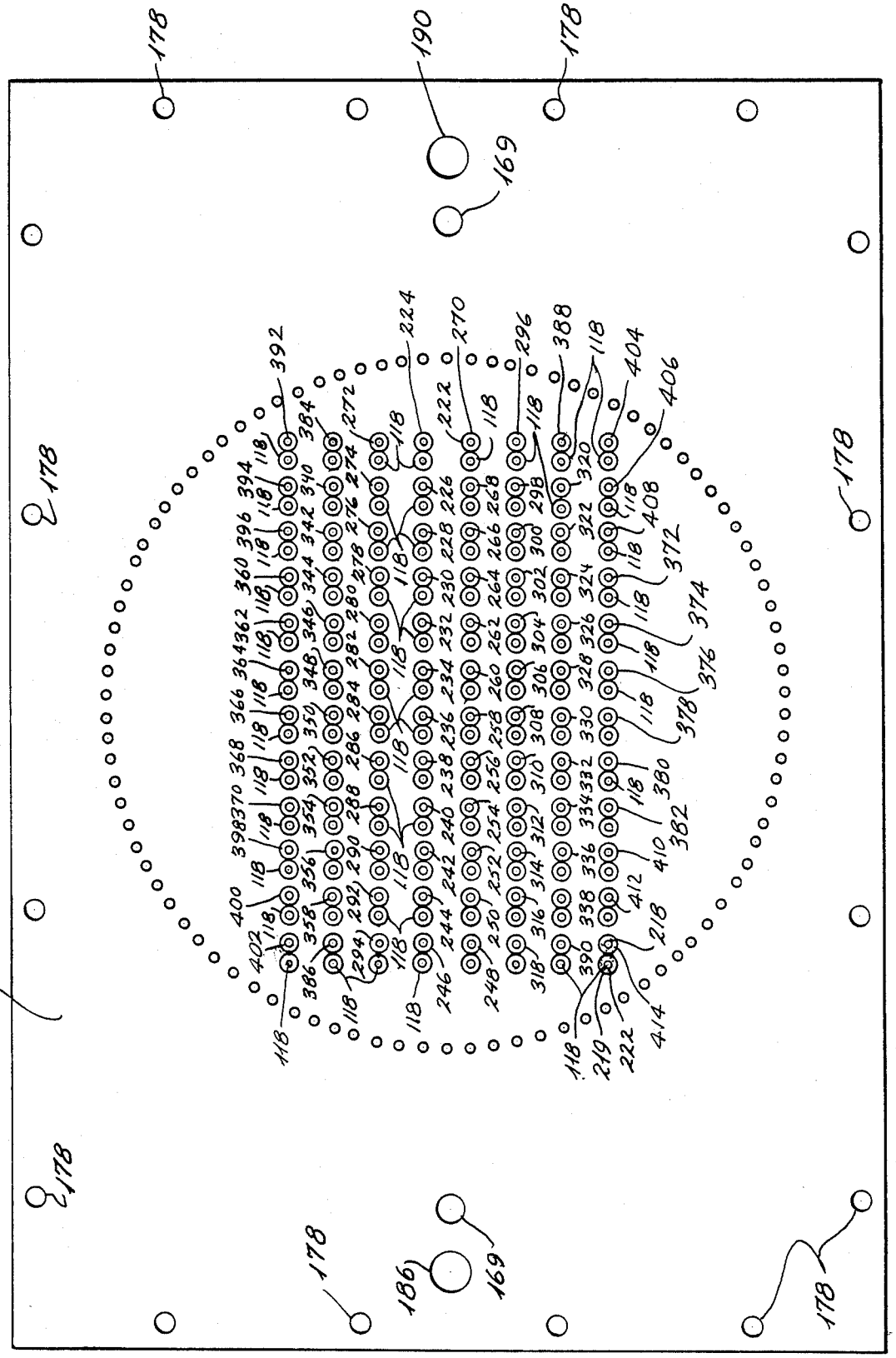

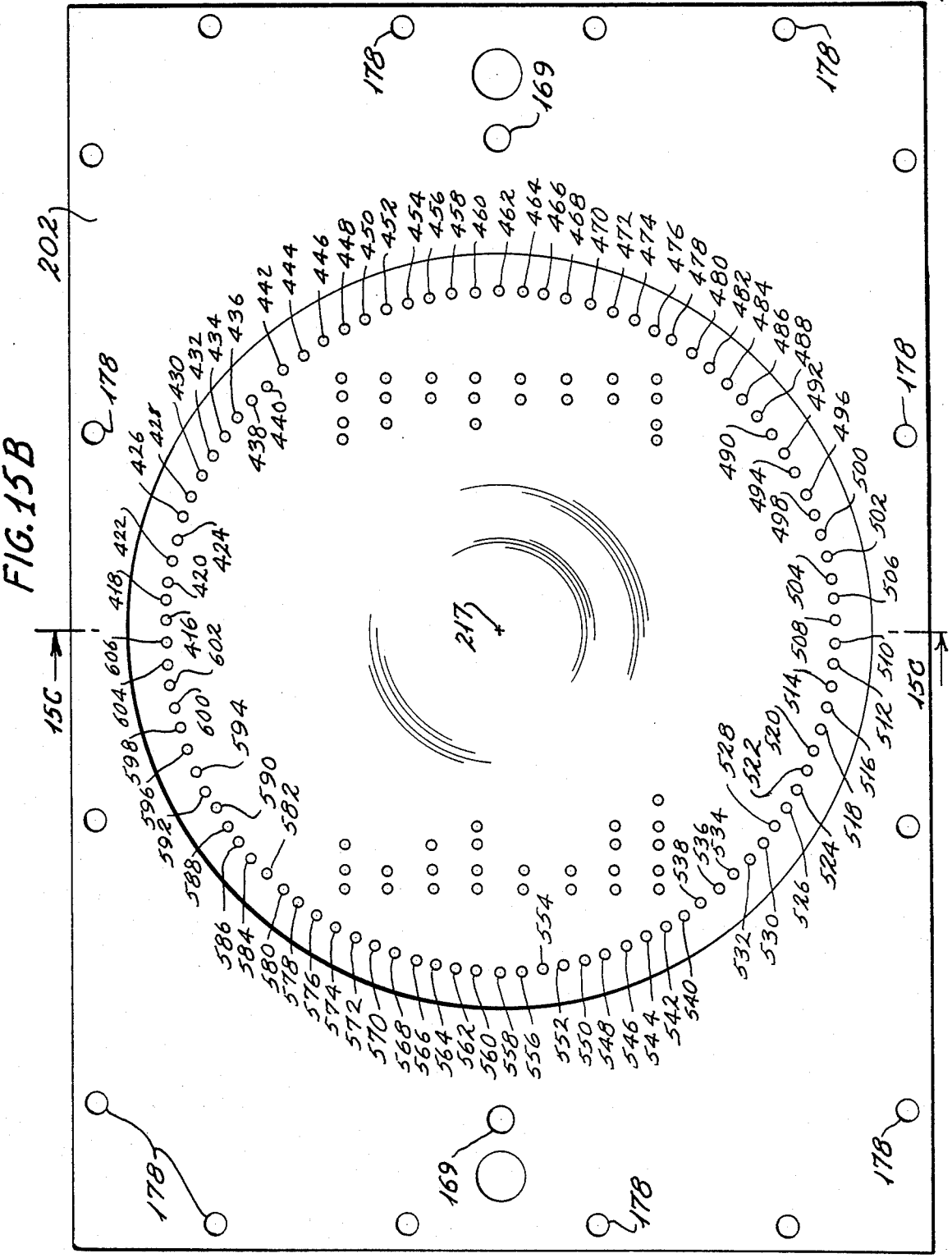

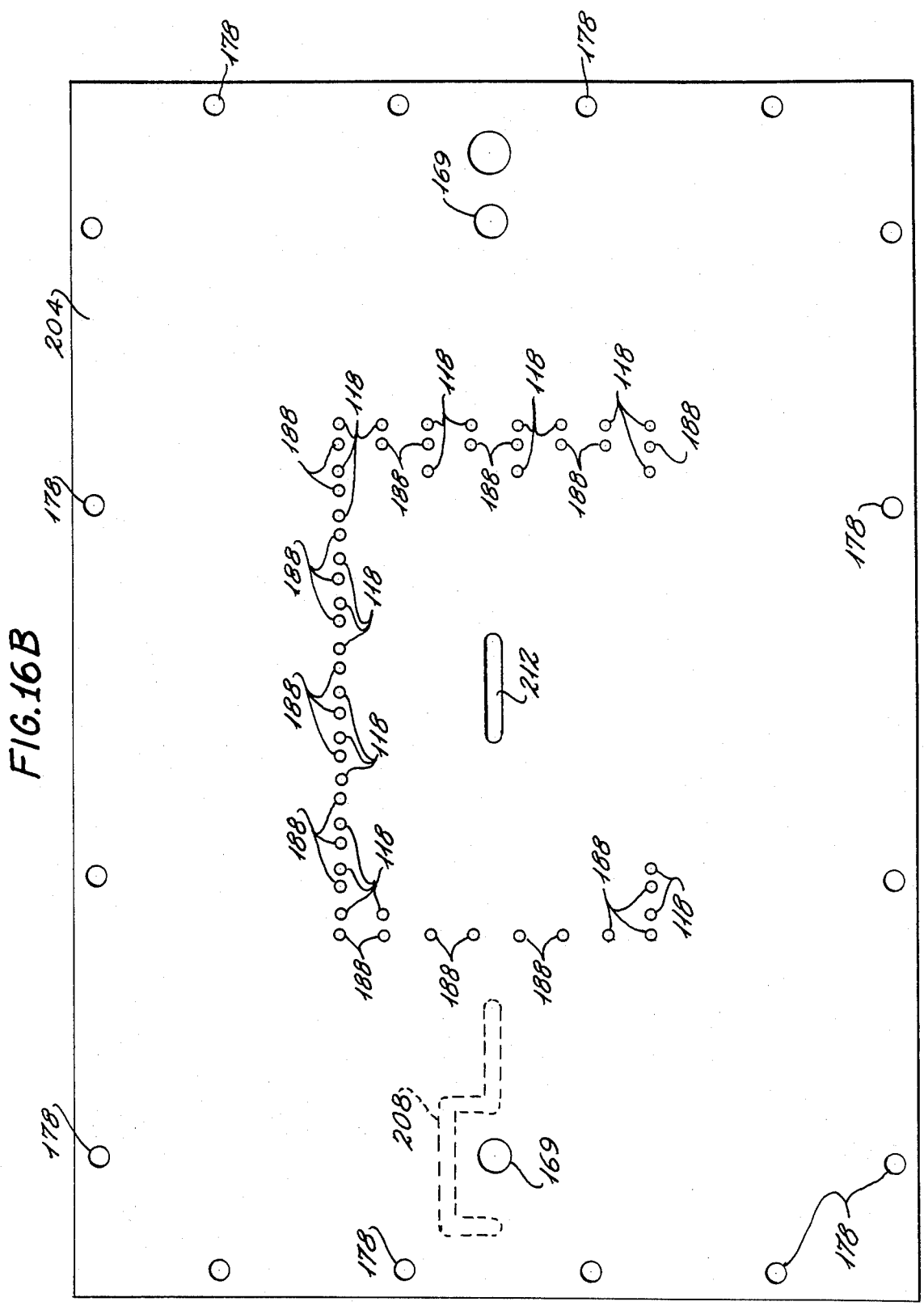

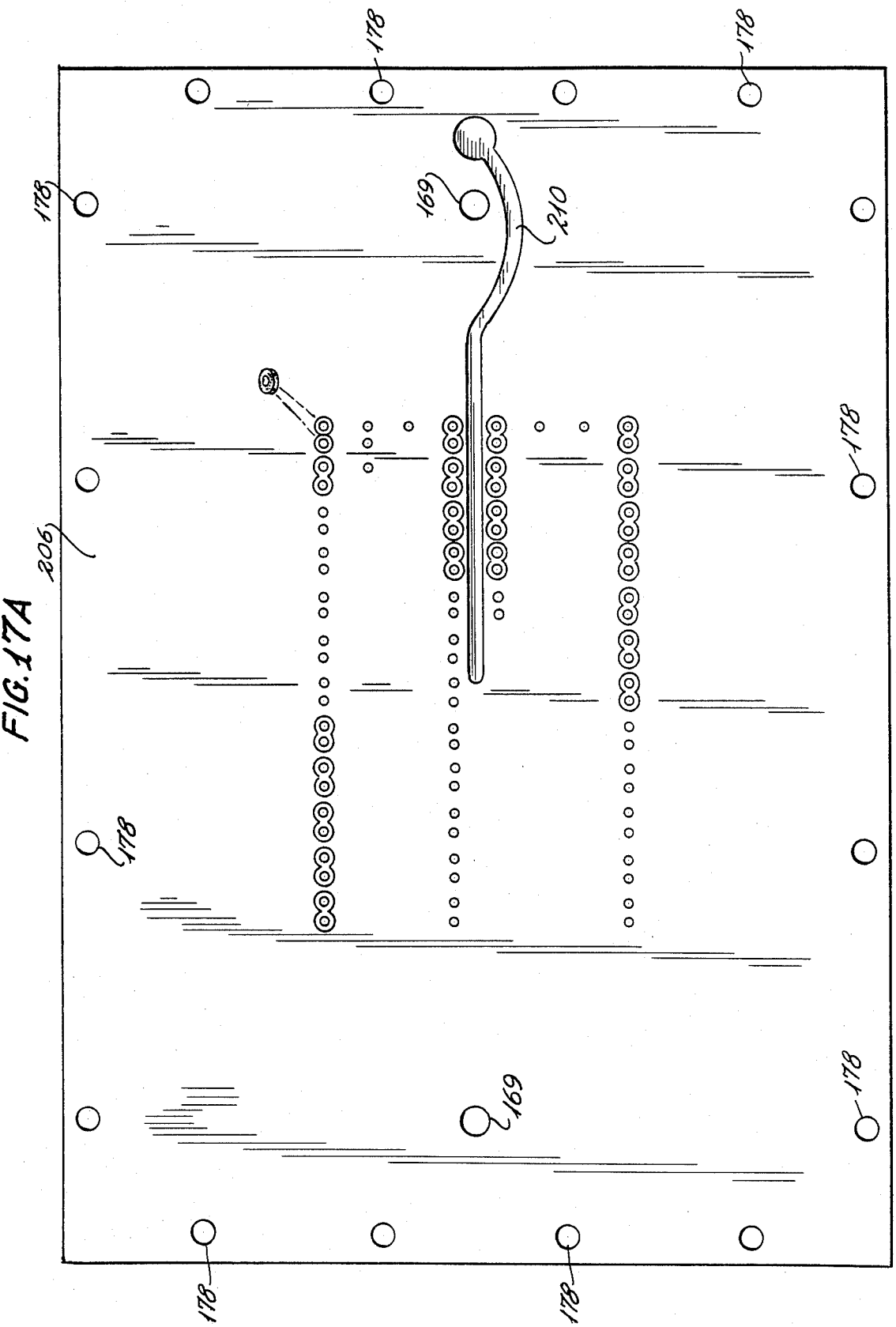

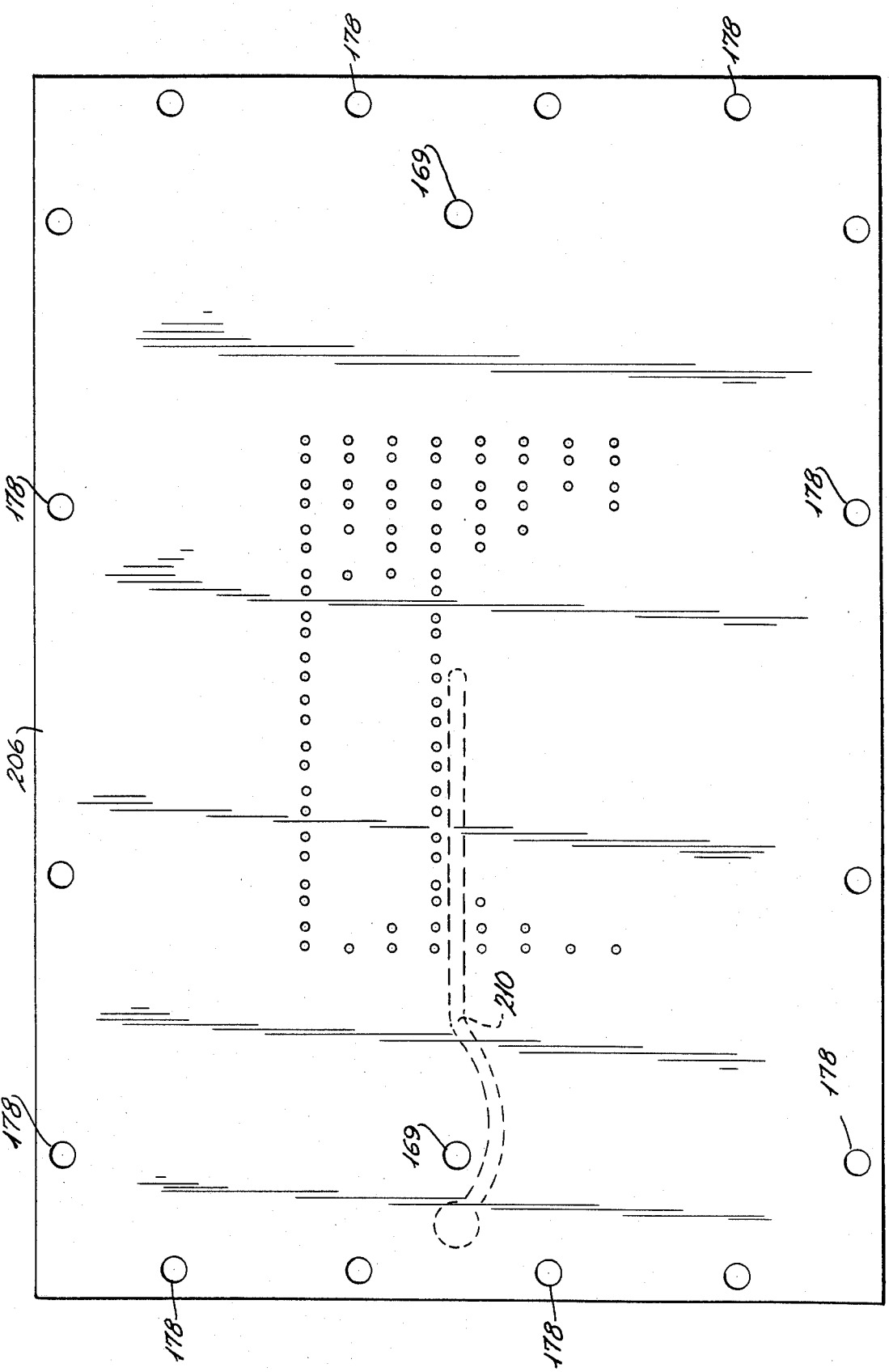

TUBELESS CELL HARVESTER

BACKGROUND OF THE INVENTION

1. Field of the Invention

The invention pertains to a multi layered cell harvester formed from a plurality of flat substantially rectangular layers having channels and passages that interconnect a paired set of wash and sample removal needles for automatically removing and harvesting cells from a plurality of test tubes or cells containing small amounts of liquid arranged in standard 96, 48 or other test tube arrangement of arrays. More particularly the invention pertains to a novel multi layered cell harvester which automatically removes cells from standard test tube racks using a plurality of sample removal needles then washes each of the test tubes by adding a controlled volume of wash fluid to each of the test tubes through a plurality of wash or reagent addition needles and then removes the wash fluid or reagent from each of the test tubes through the sample removal needles. The invention is particularly adapted to applications where the precise volumetric addition of reagents or wash fluids must be critically controlled in an array of test tubes or cells containing small volumes of fluid.

The invention provides for the precise and equivalent distribution of reagents or wash fluids to all test tubes in an array by equally adding fluid to each test tube irrespective of its position in the array by volumetrically maintaining equivalence between each of the test tube in the array. The volumetric equivalence between the test tubes in the array is provided by maintaining an equivalent length of channels from a reservoir to the tip of each wash needle, or increasing the diameter of some of the channels or by a combination of length and diameter of the channel to provide an equal volumetric addition of fluid to each test tube irrespective of its position in the test tube rack or array.

The invention is particularly suitable to applications where precise amounts of wash fluids or reagents must be precisely controlled or where small volumes of sample containers are disposed in an array or test tube rack which would overflow if a precise control of the wash fluid or added reagents were not controlled. The invention is therefore particularly advantageously adapted to a large number of small test tubes in a standard 96 or 48 test tube rack. The standard 96 or 48 test tube rack for harvesting of cells measures about 5 inches (12.8 cm) by about 3¼inches (8.3 cm). The standard test tube array used in the standard 96 test tube rack is arranged in 8 rows each containing 12 small test tubes which measure about 2 inches long (5.1 cm) having a diameter of about ¼ of an inch (6 mm) with a center distance of about ⅜th of an inch (1 cm) in which cells are placed in various fluids or mother liquids to evaluate their response to a variety of drugs and pharmaceutical preparations that in some cases include radioactive tagging agents.

The standard procedure is to remove the contents of each of the small test tubes and filter the contents of each of the small test tubes onto a sheet of filter paper having 96 separate circular areas of about ½ of an inch in diameter (1.3 cm). The samples from the 96 test tubes from the standard array are disposed in 96 separate ½inch (1.3) circular areas on a filter paper measuring approximately 9¾ (24.5 cm) by 6¾inch (17.3 cm). The sheet of filter paper containing the 96 separate ½ inch circular areas after filtration and washing the test tube samples onto the paper is subsequently cut and cultivated, placed in scintillation readers or otherwise treated to determine the efficacy of the various pharmaceutical preparations.

In operation it is important that cross contamination of the samples is avoided and separation of the samples is maintained as well as in some cases saving the mother liquid and wash reagents. As is known to those skilled in the art, the manual steps of removing, filtering and maintaining the segregation of the filtered sample and the washing of the sample out of the test tubes is a laborious and expensive process. The process can not only be expensive but dangerous to employees since some of the materials are hazardous and the possibility of contamination of the laboratory personnel is increased by the number of manipulative steps required in washing samples out of the test tubes and cleaning of the cell harvesting apparatus after each operation.

The present invention not only reduces these steps by automatically filtering and washing cell cultures from an array of test tubes but also effectively and automatically maintains the volume of wash fluids or reagents to each of the test tubes to prevent them from overflowing while maintaining the segregation of the filtered samples from the test tube onto the ½ inch (1.3 cm) areas on the filter paper. The apparatus of the invention is readily adaptable to robotic operation and eliminates much of the tubing and external apparatus that are conventionally employed in the laboratory that can increase the risk of contamination of employees when the hoses or apparatus require maintenance or cleaning The apparatus of the invention can be easily sterilized chemically or by radiation or can be sterilized by heating in an autoclave when the multi-layered cell harvester is made out of metal.

2. Description of the Prior Art

The prior art includes a variety of available filtration apparatus and devices for harvesting cell cultures. The available devices have expedited and automated a lot of the laboratory procedures involved in removing samples from large volume laboratory test tubes and racks but have still required a number of operative steps by the laboratory technician to remove the samples and if necessary save the wash reagents and mother liquid while making certain to completely remove and wash out the contents of the test tube which can be critical to determine quantitative results in binding studies. Some of the prior art devices have used vacuum sources which required turning over the test tubes, separate washing steps or the utilization of special handling equipment to change from large volume test tubes to the small volume test tubes used in standard test tube racks to provide a full ½ inch (1.3 cm) filtering area for the sample. Small volume test tubes are generally preferred in biological studies in view of costs of reagents and availability of compounds which then should be filtered on a ½ inch (1.3 cm) filter area that can be cut from the filter paper and subsequently used in cell scintillation studies, read on scintillation readers or otherwise processed.

The standard and preferred arrangement for the harvesting of cells employs a 96 or 48 test tube rack with test tubes about 2 inches long (5.1 cm) with a ¼ inch (6 mm) diameter opening arranged in 8 rows. In some cases these test tubes are connected to one another in columns of twelve test tubes to provide a column of twelve test tubes measuring about 4 inches long (10.6 cm). The length of each test tube is about 2 inches long (5 cm), with a diameter of about ¼ of an inch (6 mm) with the center distance between each of the tubes being about ⅜ths of an inch (1 cm) in each row. The rows are generally separated from one another by about ⅜th of an inch (1 cm) to form a substantially rectangular 96 test tube array. Sometimes only 4 rows of these 12 column test tubes are used in the 96 test tube rack or a special 48 test tube rack can be employed. In all such arrangements the samples must be removed and filtered and the test tubes precisely washed with an equal volume of wash fluid or reagent.

The problem is to remove the samples from each of the test tubes in the array, provide an equal volume of wash fluid or reagent to each of the test tubes irrespective of its position in the array to assure all of the sample is removed from the test tube and filter the contents of each of the test tube onto a circular ½ inch (1.3 cm) area. These circular areas containing the filtered culture are subsequently cut out and placed in a circular vials of greater than ½ inch diameter (1.3 cm) for further binding studies, read on scintillation counters or further processed according to the required studies.

Many of the available prior art devices require numerous operational steps for the removal of samples from the small tubes before filtering the contents of the test tubes on the ½ inch diameter (1.3 cm) areas of the filter paper as employed in pharmaceutical studies. A number of devices are available in the prior art which similarly provide a means for removing cells from test tubes but do not use a full ½ inch diameter (1.3 cm) filtering area but instead use a filtering area of about ¼ inch in diameter (6 mm). These nonstandard systems have developed as a result of the difficulty in removing, washing and filtering samples from a standard 96 rack array having test tubes of the size heretofore described.

Many other prior art systems have utilized larger test tubes and racks in an effort to simplify the filtering and handling of cell cultures at the expense of utilizing greater quantities of reagents and pharmaceutical compounds that many times are available in limited quantities and made specially for cell binding studies. The trade off in the prior art has generally been in favor of the utilization of small test tubes and quantities of material at the expense of the extra procedural and manipulative steps required to effectively remove, wash and filter the samples. Large test tubes have not been favored because even through they are more easily handled and washed, they require greater amounts of reagents, compositions and tissues in order to complete the binding studies.

The present invention is applicable to both large and small test tubes but is particularly amenable to small test tube since it volumetrically controls the amount of wash fluid introduced into each test tube irrespective of its position in the test tube rack. This precise volumetric control prevents one or more tubes at the center of the test tube rack from overflowing with wash fluid or added reagent while test tubes at the periphery of the rack are only partially filled. The invention provides a critical control on the amount and even distribution of wash fluid to all of the test tubes in the rack irrespective of their position in the test tube rack.

Representative of prior art showing the utilization of a standard 96 test tube rack and the dispensing of fluid into the rack is Lancaster U.S. Pat. No. 3,650,306 which describes the problem of providing an automatic sampling and dispensing apparatus capable of precisely and simultaneously withdrawing into a plurality of needles or pipettes a predetermined reproducible microquantity of liquid from a liquid source and delivering the same to a plurality of corresponding wells in a micro-titration plate. This patent pertains to a laboratory dispensing apparatus and does not pertain to a system for simultaneously withdrawing the samples from the test tubes, filtering the samples on ½ inch (1.3 cm) diameter area on a sheet of filter paper and subsequently washing the test tube and the probes or needles for withdrawing the test tube samples. This patent demonstrates the problem of accurately dispensing a precise microquantity of liquid in each of the test tubes in the array but does not teach or suggest the more important problem of removing, filtering and subsequently refilling and washing each of the test tubes.

Some of the prior art pertains to a system for washing and aspirating wash fluid from the sample. Representative of such prior art is Dodge, et al. U.S. Pat. 3,949,771 which employs a single probe for removing and providing solution to a row of four vials. Dodge, et al U.S. Pat. No. 3,949,771 provides for the removal and washing of fluids, it does not filter or employ multi-layers to replace tubing or provide a system for simultaneously removing, filtering and washing the test tubes.

Many of the prior art systems employ large test tubes such as Leder et al. U.S. Pat. No. 3,319,792 and devices for removing and filtering samples. Shepel U.S. Pat. No. 4,317,726 similarly provides a filter assembly by forming a sandwich between a cover plate and a base plate but does not automatically remove the sample from the test tube and wash the test tube.

Weinstein, et al. U.S. Pat. No. 4,245,042 like many of the other prior art devices does not employ a standard 96 test tube rack but instead employs a standard cultivation plate having two consecutive rows of twelve conventional size wells. Weinstein, et al '042 provides inlet tubes for removing and filtering samples from the test tube and outlet tubelets for washing the conventional sized wells. Weinstein, et al '042, however, most importantly, does not provide a system for volumetrically controlling the amount of wash fluid introduced to each test tube irrespective of its position in the array and does not utilize a standard 96 rack or the eight rows of twelve test tubes which require a far more precise washing and evacuation technique to remove and filter samples on a ½ inch in diameter (1.3 cm) filter area arranged on a sheet of filter paper having a size of about 9¾ inch (25 cm) by 6¾ (17.3 cm). Weinstein, et al U.S. Pat. No. 4,245,042, since it only pertains to two rows of twelve conventional size wells and a standard cultivation plate did not have the critical control problem of supplying a precise volume of wash fluid to each sample which requires the utilization of wash channels to provide a constant volume of water to all 96 test tubes to make certain the amount of water added to each test tube is the same irrespective of its position in the standard 96 test tube array.

The configuration and arrangement of the novel multi-layered cell harvester of the present invention not only provides an even distribution of wash fluid simultaneously to each of the 96 test tubes but is furthermore susceptible to robotic operation by an automatic separation of the top multi-layered block from the bottom multi-layered block coupled with an automatic feeding of new sheets of filter paper and the positioning of the filter paper between the two blocks while a new rack of 96 test tubes is introduced into the cell harvester. The novel multi-layered cell harvester includes a number of unique features which assist in the automatic removal, washing and filtering of samples while reducing the labor intensive procedures of the prior art. The novel multi-layered cell harvester further guards against contamination of the various samples while utilizing small quantities of materials from the standard 96, 48 and other test tube racks while reducing the labor, cost and time previously incident to cell harvesting operations.

SUMMARY OF THE INVENTION

The disadvantages and limitations of prior art filtering devices, liquid dispensing devices and devices for harvesting cell cultures including the problems of utilizing racks of small cylindrical test tubes of about 2 inches long (5.1) having openings of about ½ inch (1.3 cm) in diameter arranged in columns of twelve test tubes in any number of rows have been obviated in accordance with the present invention. The problems of handling, removing, filtering and washing samples from each test tube in a standard rack have been achieved by the utilization of a multi-layered cell harvester having a multi-layered top block and a multi-layered bottom block with filtration channels and wash channels for each of the test tubes in the array. The novel multi-layered cell harvester of the invention, unlike the prior art, provides an intricate series of wash channels connected to specially designed wash needles for washing the contents of each of the individual test tubes by providing an even volumetric addition of wash fluid or reagent to each test tube irrespective of its position in the rack of test tubes.

In washing each of the test tubes in the rack, care must be taken to assure that each of the small test tubes receive the same amount of wash fluid irrespective of the position of the test tube in the rack of test tubes. This objective is accomplished by the utilization of a cylindrically shaped reservoir having a conical shaped projection from the top to provide for the even distribution of wash fluid in the reservoir which is connected to each of the wash needles to provide an equal volume of wash fluid to all of the test tubes in the rack so that one or more of the test tubes at the center of the array of test tubes are not overflowing or flooded during the introduction of the wash fluid. This objective is achieved by either having the distance between the tip of the wash needle to the reservoir being of an equal distance by increasing the length of some of the wash channels where the diameter of the channel is uniform or by increasing the diameter of some of the wash channels or a combination of increasing the length and diameter of some of the wash channels.

The utilization of multi-layers to achieve a uniform distance between the tip of each wash needle to the reservoir or an increase in the diameter of the channels to various wash needles or a combination thereof combined with forming wash and sample removal channels has resulted in the elimination of the numerous hoses of the prior art required for each of the wash and sample removal needles for each sample by having the necessary tubing formed by internal channels formed within the layers. This feature allows the multi-layered cell harvester to be amenable to robotic operation and the spreading of the samples from the 96 test tube array measuring about 5 inches (12.8 cm) by 3¼ inches (8.3 cm) to a ½ inch in diameter area (1.3 cm) area on a sheet of filter paper measuring 9¼ inches (25 cm) by 6¾ in. (17.3). The spreading of the filtration channels is achieved by a set of channels for spreading the filtration channels apart before reaching the filter paper. These features of the invention not only provides for accommodation of standard filter sizes but is amenable to robotic operation and also eliminates the possibility of hoses abrading, breaking or having to be replaced and provides a more hygienic and more easily cleaned machine that can be sterilized without undue risks to laboratory personnel.

The multi-layered cell harvester of the invention is able to harvest cells from a standard 96 test tube array and separately filter each of the samples from the 96 test tubes on ½ inch (1.3 cm) in diameter areas on filter paper which can be later analyzed or cut and counted in standard counting vials. The novel multi-layered cell harvester provides for the automatic removal, filtration and washing of each of tee samples from the test tubes in the standard 96 rack array of test tubes without removing or pouring the contents of the test tubes from the rack. The novel multi-layered cell harvester is adapted to maintain the segregation of each of the filtered samples from one another. The multi layered cell harvester can be readily modified to save the mother liquid and wash fluid or added reagents from each of the test tubes. The multi layered cell harvester can also be provided with primary and secondary vacuum sources for use in alternative radioactive and non-radioactive assays.

The novel multi-layered cell harvester further includes specially formed manifolds to prevent fluids from running backward from the filter and wash fluid areas to prevent contaminating other samples and uneven distribution of wash fluids or reagents. The multi-layered top levels are held together by screws or other means and may include a vacuum or mechanical means for securing the top multi-layered level to the bottom multi-layered level. In robotic applications means such as a vacuum closing of the top multi-layered level to the bottom multi layered level assists in automated applications of the invention.

In operation the sample tray moves up to a pair of wash and sample removal needles to wash and remove samples from each of the test tubes. The tray can be activated by electrical, pneumatic or manual means. The top multi-layered level can be raised and lowered and pivotally mounted or hinged with respect to the bottom multi-layer level to allow filter paper to be robotically fed into the cell harvester between the top and bottom layers. The top layer is hinged or pivoted and lowered in a key and slot type of an arrangement to press the filter paper between the top and bottom layers. This operation activates a solenoid for a vacuum source to pull pistons from the top layer down into the bottom layer to seal the two layers together and then the samples are automatically removed from the test tubes with the sample removal needles and filtered on the filter paper and then wash fluid is introduced equally to each of the test tubes through the wash needles to wash each of the test tubes. The wash fluid can then be removed from the test tubes by the sample evacuation needles to accurately remove all the sample from each of the test tubes and any residues of the samples that remain in the evacuation channels.

The multi-layered cell harvester of the invention can be formed from any material such as metal, glass or plastic such as plexiglass, or other materials that can be processed to provide a smooth, tight fit or seal against layers and that can be cut with grooves or channels to provide sample withdrawal and wash channels.

The invention provides an efficient system for harvesting cells while providing a safe, effective and economical method of harvesting cells and cleaning the device after use. The present invention is applicable to all filtering and cell harvesting type systems for filtering and removing cells and particularly in systems using small volumes of fluid and where a standard array requires meticulous attention to the amount of fluids introduced into a multitude of test tubes in an array which because of their arrangement, requires the precise control and delivery of an equal volume of fluid to all of the test tubes. Moreover, as a consequence of its design and construction, the novel cell harvester is susceptible to robotic and automated operation and is conveniently manufactured from materials which reduce maintenance problems, prevent sample contamination and reduce the danger of exposure of laboratory personnel to hazardous materials.

DESCRIPTION OF THE DRAWINGS

Other advantages of the invention will become apparent to those skilled in the art from the following detailed description of the invention in conjunction with the accompanying drawings in which:

FIG. 4A is a top plan view of a portion of the top side of the first layer of the multi-layered top section of the novel cell harvester;

FIG. 4B is a plan view of a portion of the bottom side of the first layer of FIG. 4A;

FIG. 4C is a side view of the first layer of FIG. 4A;

FIG. 6A is a top plan view of a portion of the third layer of the multi-layered top section of the multi-layered cell harvester;

FIG. 6B is a plan view of the bottom of FIG. 6A of the multi-layered cell harvester;

FIG. 6C is a cross sectional view along the line 6C—6C of FIG. 6A;

FIG. 6D is a cross sectional view along the lines 6D—6D of FIG. of 6A;

FIG. 7A is a top plan view of a portion of the top side of the first bottom layer of the bottom section of the multi-layered cell harvester;

FIG. 7B is a plan view of a portion of the bottom of FIG. 7A;

FIG. 7C is a cross sectional view taken along the line 7C—7C of FIG. 7A;

FIG. 8A is a top plan view of the second bottom layer of the multi-layered cell harvester illustrating some of the vacuum ports partly in phantom;

FIG. 8B is a plan view of the second bottom layer of FIG. 8A of the multi-layered cell harvester illustrating several spreading channels and ports partly in phantom;

FIG. 10A is a top plan view of the fourth bottom layer of the multi layered cell harvester;

FIG. 10B is a plan view of the bottom of the fourth bottom layer of FIG. 10A of the multi-layered cell harvester;

FIG. 11A is a top plan view of the fifth bottom layer of the multi-layered cell harvester;

FIG. 12A is a top plan view of the sixth bottom layer of the multi-layered cell harvester;

FIG. 12B is a plan view from the bottom side of the sixth bottom layer of FIG. 12A of the multi-layered cell harvester;

FIG. 13A is a top plan view of the seventh bottom layer of the multi-layered cell harvester;

FIG. 14B is a plan view from the bottom side of the eight bottom layer of FIG. 14A of the multi-layered cell harvester;

FIG. 15A is a top plan view of the ninth bottom layer of the multi-layered cell harvester;

FIG. 15B is a plan view of the bottom of FIG. 15A of the multi-layered cell harvester;

FIG. 15C is a side elevational view taken along the line 15C—15C of FIG. 15B illustrating an exaggerated detail the formation of a conical shaped projection extending from the top down into the reservoir for wash fluid of the multi-layered cell harvester;

FIG. 16B is a plan view of the bottom side of the tenth bottom layer of FIG. 16A;

FIG. 17A is a top plan view of the eleventh bottom layer of the multi-layered cell harvester;

FIG. 17B is a plan view from the bottom side of the eleventh bottom layer of FIG. 17A;

DETAILED DESCRIPTION OF THE INVENTION

Figure 1:
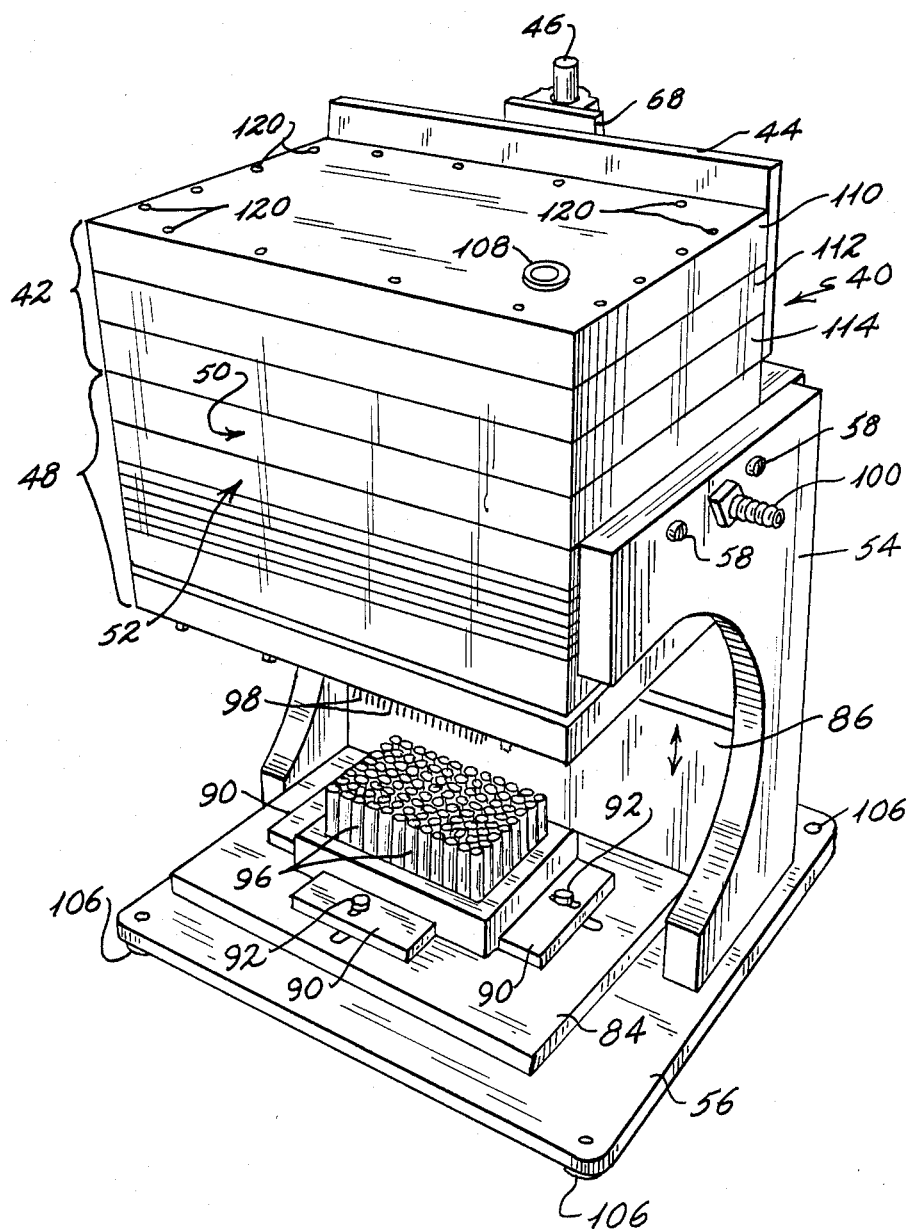
FIG. 1 is a perspective view of a multi-layered cell harvester constructed in accordance with the invention.

The invention pertains to a multi-layered cell harvester for removing, washing and filtering cells from test tubes and is particularly advantageously adapted for cylindrical or rectangular test tubes employing small or precise amounts of fluids or having small openings of about ¼ an inch (6 mm) and about 2 inches long (5.1 cm). The invention is also applicable to standard 96 plates of about ¼ inch (6 mm) in diameter and ¼ inch (6 mm) high. Standard laboratory containers also include rectangular cells and circular test tubes for which the invention may be advantageously employed. The invention provides for the removal and uniform addition by volume of wash fluid to all of the containers or test tubes in the test tube rack irrespective of their location and the removal and filtering of the samples from the test tubes by an automatically activated cell harvester susceptible to robotic adaption and operation.

The invention accomplishes its advantages by providing a uniform distribution of minute quantities of wash fluid or larger quantities where precise control of the volume of fluid is important to all of the test tubes in the test tube rack by employing a reservoir having a cone shaped projection from the top to make certain that entrained or trapped air does not erroneously fill some of the test tubes at the expense of another. The reservoir in combination with wash channels that interconnect the reservoir to the wash needles provide an equal volume distribution of fluid to all of the test tubes in the test tube rack irrespective of their position in the test tube rack. The constant volume distribution of fluid to all the test tubes is achieved by either having the distance from the tip of each wash needle to the reservoir the same or by lengthening some of the channels from the reservoir to the individual test tubes or by increasing the diameter of some of the wash channels to some of the test tubes or a combination of both.

In the preferred embodiment of the invention the equal volume of wash fluid to all of the test tubes is accomplished by maintaining the same distance from the tip of each wash needle to the reservoir. This constant distance is maintained by increasing the length of some of the wash channels to the reservoir. The length of the channel is increased through the layers and around the surfaces of the various layers of the multi-layered cell harvester. The reservoir is disposed at a level below the opening for the inlet needle so air can be purged before the wash fluid travels up through the various multiple lower layers for a distance sufficient to make the distance the fluid travels from the reservoir to the tip of each wash needle the same.

The advantages of the invention have been achieved through an extensive research investigation into the precise control of the addition and removal of small and critical volumes of fluids from various points in an array of test tubes in a test tube rack. This research investigation coupled with work on providing an automated cell harvester to decrease the exposure of laboratory workers to potentially harmful substances has resulted in a multi-layered cell harvester susceptible to robotic operation. The invention has further reduced the potential for contamination and danger to maintenance and laboratory personnel with radioactive and contagious and infectious substances.

Figure 2:
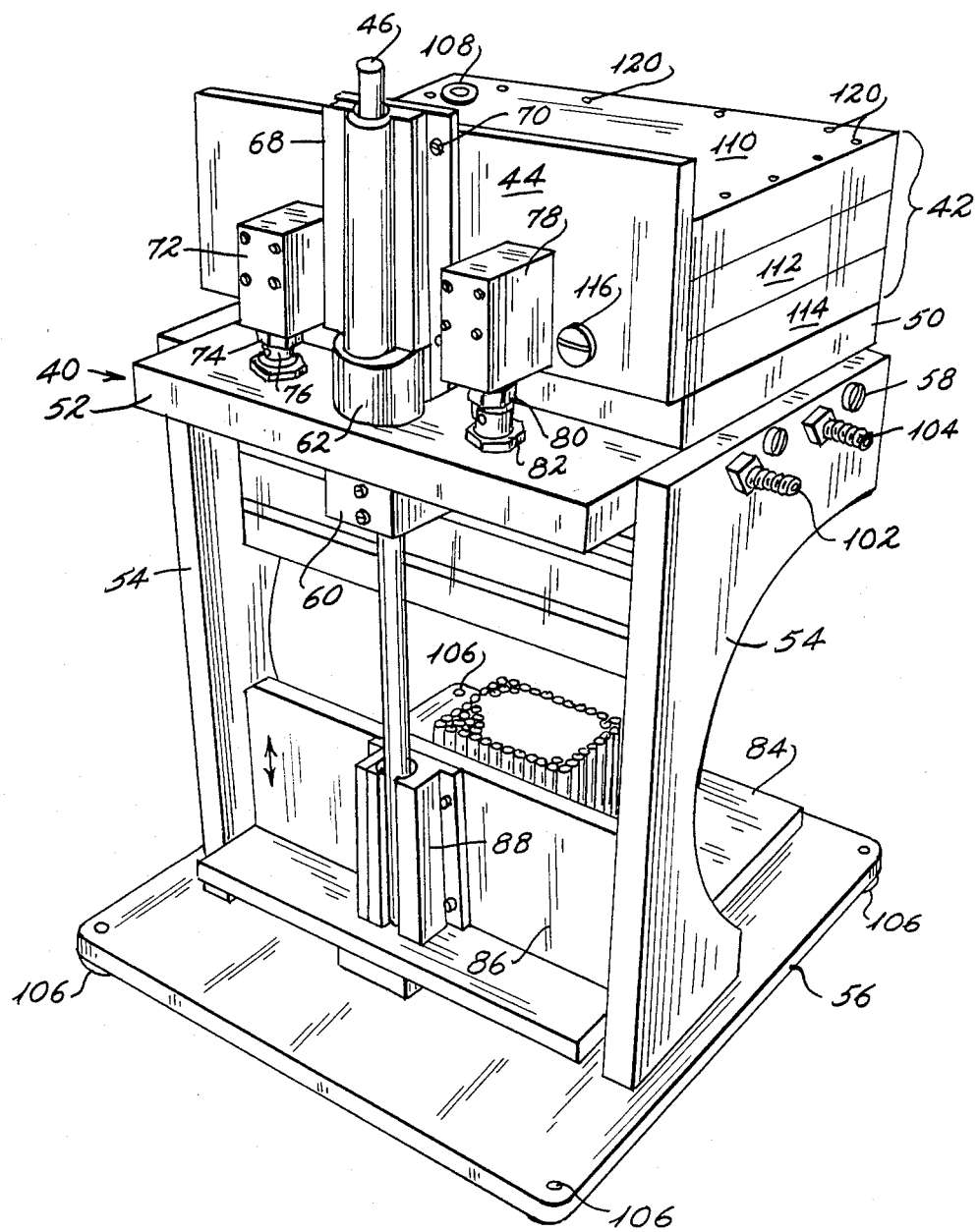
FIG. 2 is a rear elevational view of the multi-layered cell harvester of FIG. 1.

Referring now to FIGS. 1 and 2, a cell harvester 40 constructed in accordance with the invention is illustrated having multiple top layers 42 attached to a backplate 44 pivotally attached to an upright rod 46. Cell harvester 40 also includes a plurality of lower layers 48 having a filter paper support layer 50 supported by a manifold layer 52. The manifold layer 52 is supported by a pair of upstands 54 which are supported by the base 56. The manifold layer 52 is held in place by a plurality of screws 58 or other fastening means which support the manifold layer 52 which extends rearward to support the rod 46 between a clamp 60 and a collar 62 having a slot 64 (FIG. 3) for receiving a pin 66 on the backplate collar 68 which may include bearings and is attached to backplate 44 to rotatably position and fix the multiple top layers 42 with respect to the filter paper support layer 50. The backplate 44 is pivotally attached to the upright rod 46 by means of a backplate collar 68 attached to the backplate 44 by screws 70.

The backplate 44 includes a primary vacuum connection housing 72 having a detachable fitting 74 for connection and disconnection over a bayonet fitting 76 having suitable sealing means such as O-rings for connection and de-connection from detachable fitting 74. The bayonet fitting 76 terminates in a vacuum hose connection (not shown) similar to other such vacuum hose connections shown on the multi-layered cell harvester 40. The primary vacuum connection housing 72 provides a vacuum source for filtering samples in the standard 96 rack array of test tubes as will hereinafter be described in greater detail.

The cell harvester of the present invention includes an optional secondary vacuum connection housing 78 having a detachable fitting 80 and corresponding bayonet fitting 82 similar to those described with respect to the primary vacuum connection housing 72. The optional secondary vacuum connection housing 78 is provided for radioactive cell studies where solutions of radioactive materials must be separated or maintained separate from other wash and filtrate mediums.

The upright rod 46 extends down from the manifold layer 52 and is designed to support and position a movable test tube platform 84 with respect to paired sample removal and wash needles. The test tube platform 84 includes a back 86 attached to a slidable positioning sleeve 88 which positions the test tubes with respect to paired sample removal and wash needles and allows the tray to be moved either manually or robotically up and down upright rod 46 with respect to the plurality of lower layers 48. The test tube platform 84 includes a plurality of positioning jigs 90 adjusted by screws 92 to position a standard test tube rack 94 containing 96 test tubes 96 arranged in 8 rows of 12 test tubes.

Figure 3:
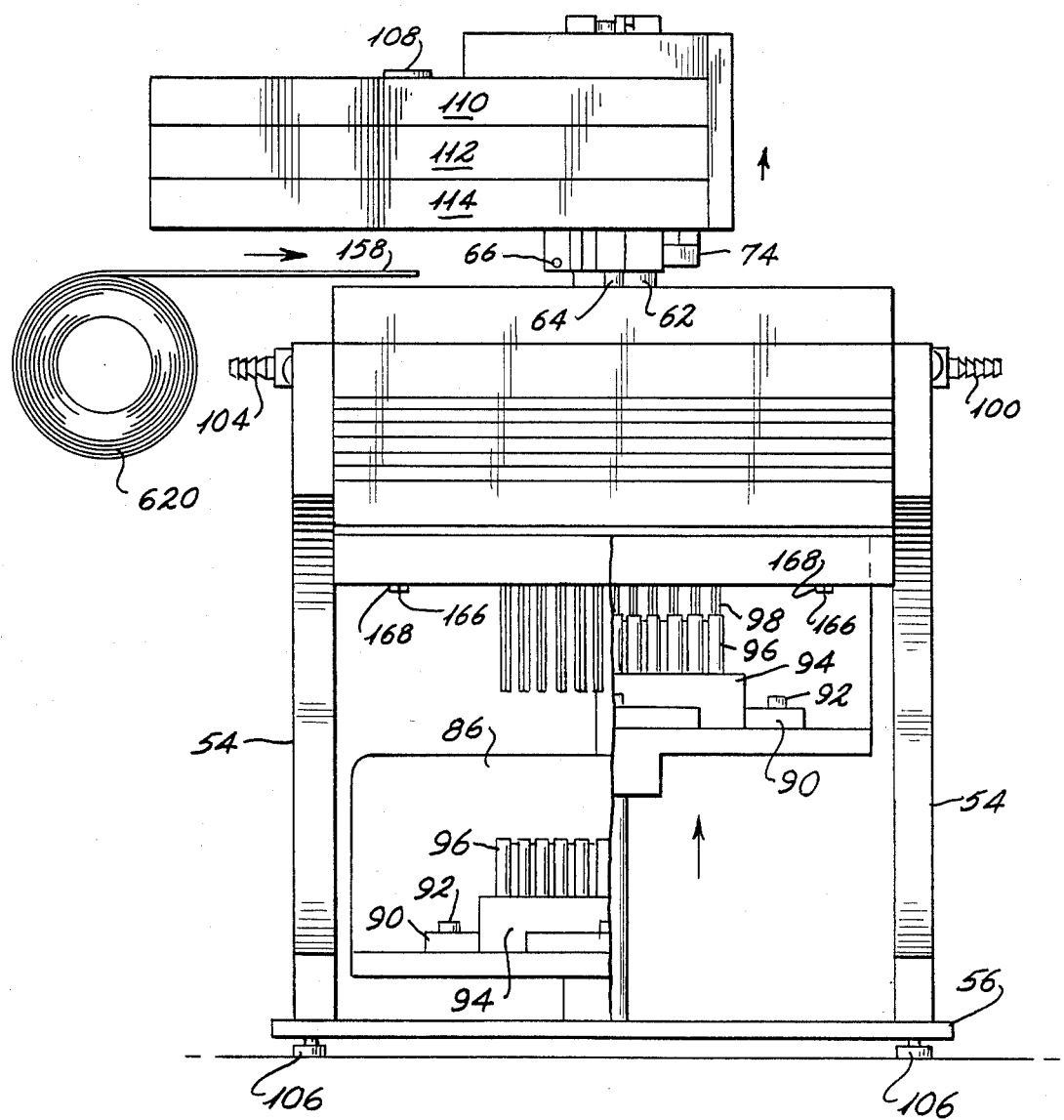
FIG. 3 is a front elevational view partly in section illustrating a robotically controlled embodiment for raising and lowering a multi-layered top section, feeding filter paper and raising and lowering the test tube array.

The raising and lowering of the entire platform 84 raises and lowers the test tubes 96 with respect to a total of 192 evacuation and wash needles 98 arranged in pairs extending from the bottom of the plurality of lower layers 48 as will be described hereinafter in greater detail. The relationship between the test tubes 96 and the pairs of evacuation and wash needles 98 in raising and lowering the test tube platform 84 is illustrated in FIG. 3. The test tube platform 84 can be raised and lowered manually and in the preferred embodiment is raised and lowered automatically with an electric motor.

The novel multi-layered cell harvester includes a vacuum port 100 (FIG. 1) connected to manifold layer 52 through one of the upstands 54 for clearing fluid from the wash manifold and preventing fluids from flowing back to the wash needles in a manner that will be described hereinafter in greater detail. The manifold layer 52 also includes a vacuu port 102 (FIG. 2) for clamping the multiple top layers 42 to the filter paper support layer 50 in a manner that will be described hereinafter in greater detail. Vacuum port 102 can be eliminated where other mechanical or physical means are utilized to clamp or fix the multiple top layers 42 with respect to the filter paper support layer 50.

The manifold layer 52 also includes a wash port 104 for supplying wash media to the wash needles 224–414. Ports 100, 102, 104 and the primary vacuum connection housing 72 and the optional secondary vacuum connection housing 78 may all be controlled by a solenoid in a manner as will be hereinafter described in greater detail to control and coordinate the operation of the novel multi-layered cell harvesters constructed in accordance with the invention.

In the operation of cell harvesters of the invention it is extremely important all of the wash fluid or reagent entering wash port 104 is precisely and accurately metered in an equal volume distribution to each of the wash needles into each of the test tubes 96. The precise metering of wash fluid to provide an equal distribution of wash fluid to all wash needles 224–414 irrespective of their position is accomplished by providing an equal volume of wash fluid or reagent from the reservoir to each of the wash needles. The equal volume of fluid to each of the wash needles can be accomplished by having all of the distances from the reservoir to the tip of each wash needle the same by lengthening some of the wash channels in the plurality of lower layers 48 or by increasing the diameter of some of the wash channels or a combination of both.

In addition to providing for an equal volume of flow of fluid to each wash needle the reservoir requires a system for preventing air and fluids from being trapped and causing uneven fluid distribution. This requires the utilization of a reservoir having an effective means for purging air before introducing wash fluid or reagents to the reservoir as will be described hereinafter in greater detail along with an arrangement of channels which provides for an even distribution of wash fluid to all of the 96 test tubes 96. This process is further assisted by making certain the multi-layered cell harvester is in a level position with respect to a work bench. This levelling is in part achieved by the utilization of adjustable legs 106 provided on the four corners of the base 56. The adjustment of these adjustable legs 106 is achieved by employing a standard level indicator 108 (FIG. 1) provided in the top layer 110 of the multi-layer cell harvester 40.

The multiple top layers 42 include a top layer 110, a middle layer 112 and a bottom top layer 114. Bottom top layer 114 is attached to the backup)ate 44 by means of a pair of screws 116. Each of these layers are held closely together with screws 120 and both the top as well as the bottom layers, are made of plastic such as plexiglass, metal or some other suitable substance that can be machined to a fine flat tolerance to prevent the migration liquids or leakage of fluids from between the various layers.

Figure 18:
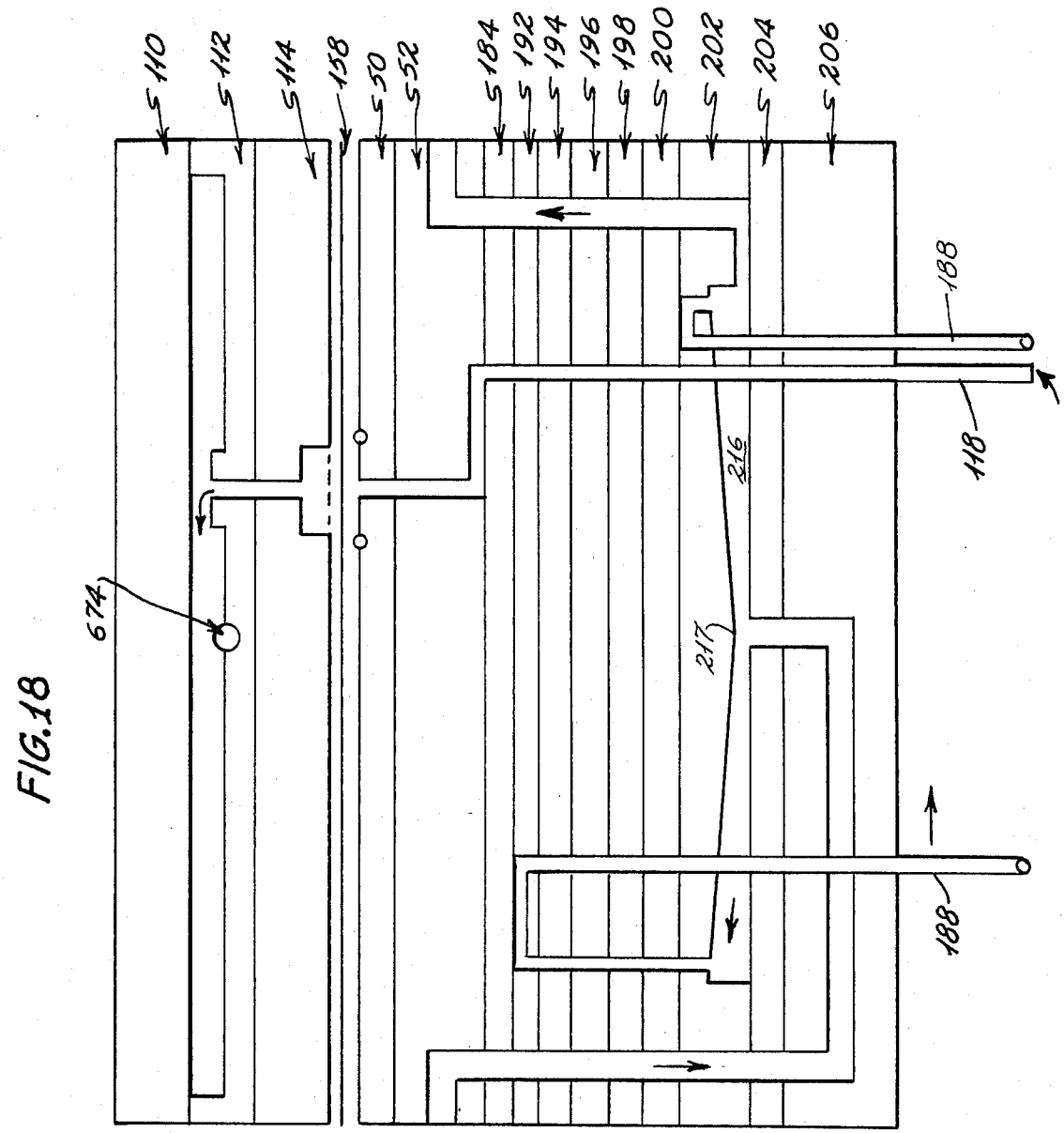
FIG. 18 is a schematic ide elevational view illustrating in exaggerated detail the major components and depicting flow patterns for the multi-layered cell harvester.

Referring now to FIGS. 1, 2, 4A, 4B, 5A, 5B, 5C, 6A, 6B, 6C, 6D and 18 the construction and arrangement of the components of the multiple top layers will be described in relation to the 96 evacuation needles 118 (FIG. 18). The top layer 110 as well as the other layers in the preferred embodiment are made of plexiglass that has been made sufficiently flat as to prevent leakage between the layers. If desired a suitable sealing means can be added between the various layers. The top layer 110 (FIG. 4A) includes a standard level indicator 108 for levelling the multi-layered cell harvester 40 as heretofore described. The layer 110 includes a plurality of screws 120 and holes 122 for fastening top layer 110, middle layer 112 and bottom top layer 114 together.

Figure 5C:
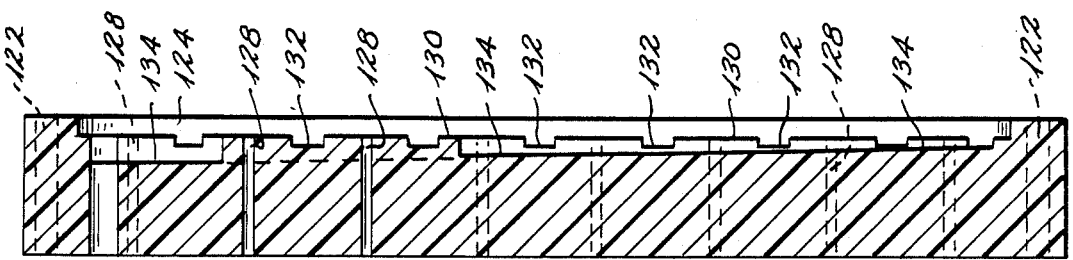
FIG. 5C is a cross sectional view taken along the lines 5C—5C of FIG. 5A.
Figure 5B:
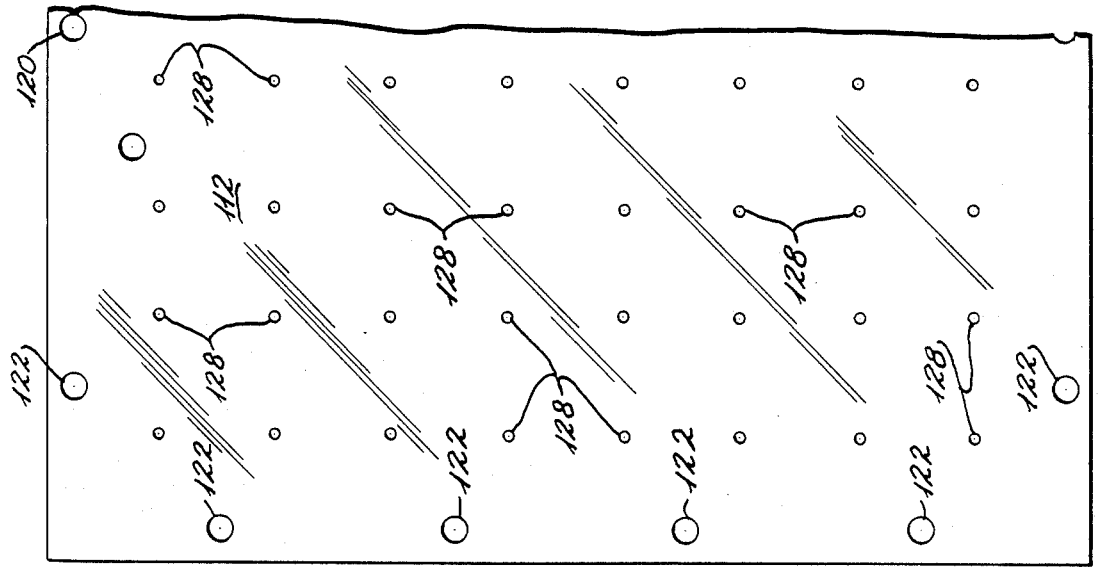
FIG. 5B is a plan view of the bottom side of a portion of the second layer of FIG. 5A.
Figure 5A:
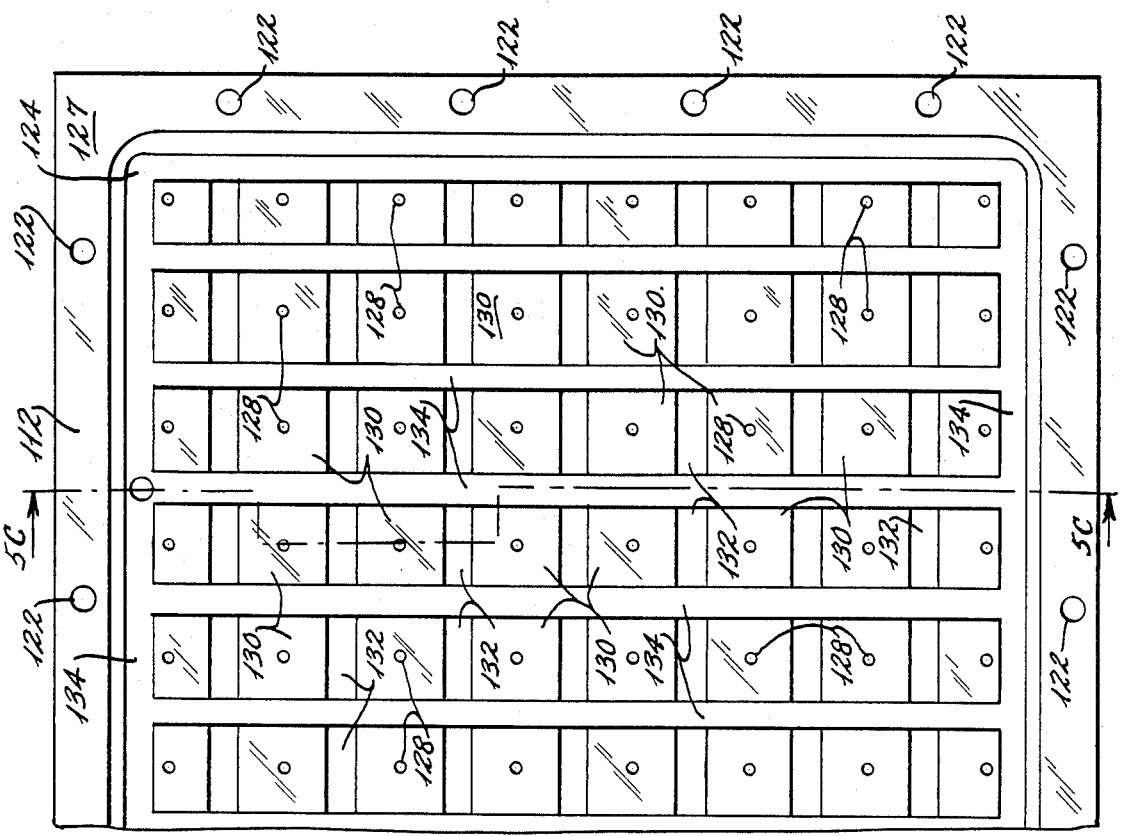
FIG. 5A is a top plan view of the top side of a portion of the second layer of the multi-layered top section of the multi-layered cell harvester.

The bottom side of top layer 110 (FIG. 4B) together with middle layer 112 forms a vacuum manifold. This manifold is formed between the top layer 110 and middle layer 112 by providing a recess 124 which can be sealed by a slightly raised rectangular ridge 126 and the contacting of respective surfaces 125 and 127 (FIG. 4B and 4C) of top layer 110. The manifold created communicates with 96 evacuation holes 128 in middle layer 112 corresponding to the 96 evacuation needles 118 (FIG. 18) and the 96 test tubes 96. On the top side of middle layer 112 a plurality of cubic shaped projections 130 surround each of the evacuation holes 128 and form a plurality of channels 132 and deeper grooves 134 or the grooves may be slanted toward the outlet port (FIG. 5A). The purpose of the cubic shaped projections 130 surrounding each of the holes 128 in combination with the channels 132 and deeper grooves 134 is to prevent any fluid which has been evacuated from evacuation needles 118 from flowing back through the layers into the test tues 96 after the filtration and washing the 96 test tubes 96. The channels 132 and deeper grooves 134 are connected to the primary vacuum connection housing 72 or the secondary vacuum connection housing 78 through holes provided in backplate 44.

The evacuation holes 128 in middle layer 112 communicate through middle layer 112 to and through bottom top layer 114 (FIG. 6A and 6B). Bottom top layer 114 is secured in place to backplate 44 by screws 116 which are screwed into bottom top layer 114 in threaded recess 136. The bottom top layer 114 includes a plurality of pistons 138 which extend through bottom top layer 114 through holes 140 having an enlarged opening 142 to accommodate an O-ring 144 disposed on the top end of pistons 138. Pistons 138 each include a piston head 146 and a further O-ring 148 for being drawn down into and sealing bottom top layer 114 to filter paper support layer 50 (FIG. 7A).

The application of vacuum to vacuum port 102 draws the plurality of pistons 138 down into bottom top layer 114 to seal each of the pistons 138 and O-ring 144 in bottom top layer 114 against filter paper support layer 50 (FIG. 8A) by forcing pistons 138 into corresponding holes 140 which communicate through filter paper support layer 50 to a manifold created by the plurality of grooves 150 in manifold layer 52 (FIG. 8A). The clamping of the multiple top layers 42 to the plurality of lower layers 48 can be achieved through vacuum or through mechanical means. In the preferred embodiment a vacuum has been utilized since it enhances the robotic application of the invention as will be described hereinafter in greater detail.

The plurality of the evacuation holes 128 terminate in a cone shaped recess 152 (FIG. 6D) on the bottom side of bottom layer 114. The cone shaped recess 152 further terminates in a cylindrical opening 154 which is designed to accommodate a plurality of circular screens 156 of about ½ inch (1.3 cm) in diameter. The purpose of the circular screens 156 is to provide individual screen support and backing to a sheet of filter paper 158 (FIG. 3) placed in between bottom top layer 114 and filter paper support layer 50.

The filter paper support layer 50 (FIG. 7A) includes 96 evacuation holes 128 corresponding to the 96 test tubes 96 in rack 94. Each of the evacuation holes 128 is surrounded by a circular recess 160 which is designed to accommodate an O-ring seal 162. The purpose of the O-ring seal 162 is to provide a tight seal between the underside of filter paper 158 which is sandwiched between each of the circular screens 156 of bottom top layer 114 and filter paper support layer 50. The circular O-rings are about ¾th of an inch in outside diameter (1.9 cm) with about a 9/16 of an inch (1. cm) inside diameter to provide a full ½ inch (1.3 cm) filtering area for each of the samples in the 96 test tubes in rack 94.

The filter plate paper support layer 50 includes a plurality of threaded holes 164 for receiving a plurality of threaded screw bolts 166 for tightly compressing each of the plurality of lower layers 48 together. As with the multiple top layers, it is important that the plurality of lower layers 48 are machined as flat as possible to make certain that the contacts between plates are as close as possible to prevent leakage between the manifold, reservoir, holes and channels provided in the various plurality of lower layers 48. The layers are held together by bolts 166 threaded at one end into filter paper support layer 50 and held in place at the other end by screws 168 (FIG. 3).

The manifold layer 52 supports filter paper support layer 50 and is attached to upstands 54 by employing screws 58 as heretofore described. The screws 58 that attach upstands 54 (FIG. 2) to manifold layer 52 are threaded into threaded holes 170 (FIG. 8A) in manifold layer 52. Manifold layer 52 includes opening 172 to accommodate vacuum port 102 and wash opening 174 to accommodate wash port 104. Manifold layer 52 also includes a vacuum opening 176 to accommodate vacuum port 100 to clear fluids from the wash manifold to prevent the needles from dripping and to purge the system from fluids that might otherwise cause fluids from remaining in the wash channels and dripping to cause additional amounts of fluid to be added to some of the test tubes 96 in rack 94 and thereby interfere with the precise introduction of a constant volume of fluid to each of the test tubes 96.

Manifold layer 52 also includes a plurality of holes 178 for accepting bolts 166 to position and hold together the plurality of lower layers 48. Lower layer positioning holes 169 may be provided in the multiple layers to assist in the alignment of the various lower layers. Manifold layer 52 also includes the plurality of the evacuation holes 128 for connecting the manifold layer 52 with the evacuation needles 118 with the 96 test tubes 96 in rack 94. The manifold layer 52 includes a hole for the collar 62 and bolts 171 for holding collar 62 in place (FIGS. 3 and 8A). The collar 62 holds upright rod 46 in place and includes a slot 64 for receiving a positioning pin 66 in place for positioning the multiple top layers 42 with respect to the plurality of lower layers 48. The collar 62 and positioning pin 66 also maintains the multiple top layers 42 at a predetermined distance from the plurality of lower layers as the multiple top layers are pivoted with respect to the lower layers. Manifold layer 52 also includes opening 172 for carrying bayonet fitting 76 and opening 175 for receiving bayonet fitting 82.

Figure 9:
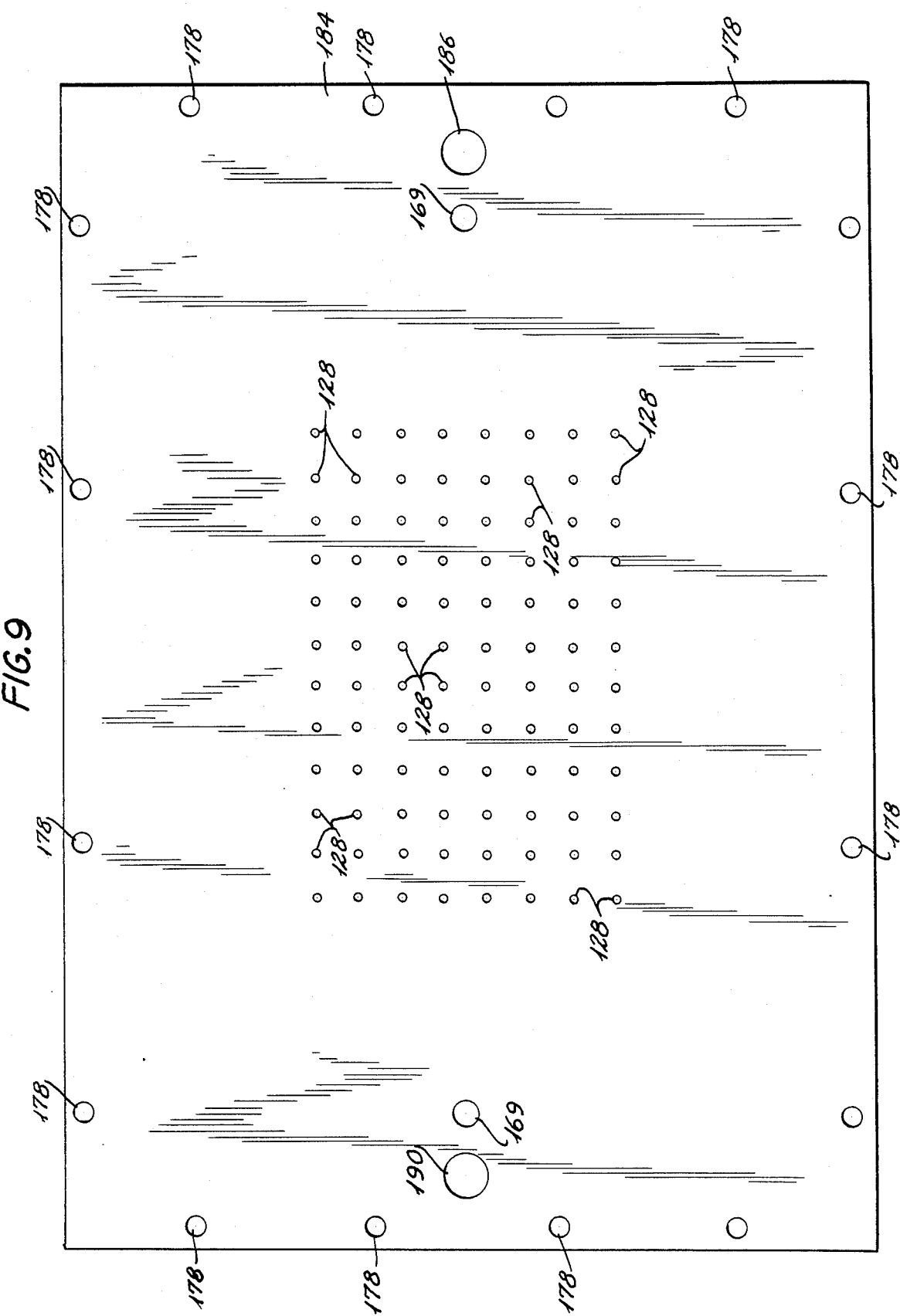
FIG. 9 is a top plan view or a bottom plan view of the third bottom layer of the multi leveled cell harvester, the top and bottom being substantially identical.

Manifold layer 52 on the bottom side (FIG. 8B) includes a clamp 60 for receiving and securing upright rod 46 in place in the multi-layered cell harvester 40. Clamp 60 is held in place by a plurality of screws 180 for holding the clamp and upright rod 46 securely in place. The bottom side of manifold layer 52 also includes a plurality of channels 182 for re-positioning each of the evacuation holes 128 corresponding to the test tubes 96 in the test tube rack 94. The channels 182 essentially reposition or spread holes 128 from their position corresponding to their position in relation to the 96 test tube rack which corresponds to the positions as shown in the third layer 184 (FIG. 9) of the multi-layered cell harvester to the filter area inside each circular recess 160 to provide a full ½ inch (1.3 cm) circular filter area on the filter paper. In FIG. 9 the evacuation holes 128 correspond directly to the position of the centers of each of the test tubes 96 in rack 94. These evacuation holes 128 are connected to the evacuation needles 118 for removing samples from the 96 test tubes in the standard rack 94.

Wash opening 174 in manifold layer 52 provides an inflow of wash fluid, which communicates with wash fluid hole 186, which communicates through third layer plate 184 which subsequently communicates with a wash reservoir and the wash needles 188. Manifold layer 52 also includes opening 176 communicating with vacuum port 100 which communicates through third layer plate 184 through vacuum hole 190 and subsequently to the wash reservoir and the wash needles 188 to remove trapped wash fluid or reagent from the system to prevent entrained fluid from inadvertently being added to some of the test tubes 96 and thereby allowing some of the test tubes to receive a greater volume of liquid than others.

Referring now to FIGS. 10A through FIG. 18, the arrangement and distribution of the wash needles 188 and the evacuation needles 118 in the operation of the multi-layered cell harvester will be described in greater detail. As can be seen from the figures, the fourth layer 192, fifth layer 194, sixth layer 196, seventh layer 198, eighth layer 200, ninth layer 202, tenth layer 204 and eleventh layer 206 each include holes 178 for receiving bolts 166 for holding each of the layers together. Each of the layers 50, 52, 184, 192, 194, 196, 198, 200, 202, 204 and 206 are machined as flat as possible to maintain close contact between the layers and prevent leakage of fluids from between the layers. As heretofore discussed, these layers may be clamped sealed or otherwise attached in close contact with one another in accordance with the invention. In the preferred embodiment the layers are bolted together to allow the layers to be taken apart to allow the cell harvester of the invention to be more easily cleaned and sterilized by chemicals or radiation and where the layers are made of metal to be disassembled and autoclaved.

As can be seen from FIGS. 10A to 18 each of the layers 192, 194, 196, 198, 200, 202 include both a wash fluid hole 186 and a vacuum hole 190. Layer 204 (FIG. 16A) includes a wash fluid hole 186 but does not include the vacuum hole 190. Instead the vacuum hole 190 terminates in tenth layer 204 in a groove 208. Wash fluid hole 186 similarly terminates in a wash groove 210 in eleventh layer 206 which communicates through a slot 212 in tenth layer 204 to supply wash fluid or reagents to the reservoir provided between ninth layer 202 and tenth layer 204 (FIG. 15B and 16A). The reservoir 216 (FIG. 18) formed between layers 202 and 204 provides an equal volume of wash fluid or reagents to wash needles 188 and each of the test tubes 96 irrespective of their position in rack 94 as will be described hereinafter in greater detail.

In accordance with the invention it is critically important to make certain all of the 96 test tubes 96 receive the same volume of wash fluid at the same time. This may be assisted by the utilization of an air purge means in reservoir 216 which evenly purges air out of the reservoir to all of the wash needles 188 before wash fluid or reagent is introduced into reservoir 216. This can be accomplished by employing a slight conical projection 217 extending down into reservoir 216 as shown in FIGS. 15C and 18. The cone shape projection 217 in reservoir 216 promotes the even distribution of wash fluid to all of the wash needles 188 and assures that air trapped in the system is equally dispersed to all of the test tubes 96 so as to not interfere with the constant volume of wash fluid provided to each of the wash needles 188.

The control of volume of water to all of the test tubes 96 in the rack 94 is so important where precise metering of wash fluids is required that vacuum hole 190 which is connected to vacuum port 100 is utilized to evacuate reservoir 216 after each introduction of fluid to reservoir 216 to prevent the wash needles 188 from dripping into the test tubes 96 and from preventing fluids from becoming trapped in the wash channels and thereby interfere with the introduction of a constant volume of fluid to each of the test tubes 96. In the preferred embodiment reservoir 216 and each of the wash channels and needles are automatically cleared between each addition of wash fluid or reagent by the solenoid control of the vacuum port 100.

The invention provides for the evacuation of reservoir 216 wash needles 188 and their interconnecting wash channels to make certain fluids left in the reservoir wash needles or channels do not drip back into the test tubes 96 or result in the unequal volumetric addition of fluids to some of the test tubes 96 at the expense of others. The precise control for the addition of wash fluids and reagents is further achieved by the conical shaped projection 217 which causes wash fluids or reagents added through slot 212 to enter reservoir 216 to evenly distribute air and then wash fluid out radially to wash holes 416 to 606 (FIG. 15B) into the wash channels and corresponding wash needles 224-414

The even distribution of an equal volume of wash fluid or reagent to each of the wash needles 188 irrespective of their position in test tubes 96 is further accomplished by making certain the distance from each of the wash holes 416-608 to the tip of each of the wash needles 224-414 (FIG. 15A) is the same or by increasing the diameter of some of the wash channels to the wash needles disposed at the perimeter of the array or a combination of both increasing the length and diameter of the wash channels.

Referring now to FIG. 10A to 15B and 18 the relationship between the reservoir 216 and the wash holes 416-606, wash channels and heads 218 of the wash needles 188 disposed in ninth layer 202 is illustrated. More particularly, wash fluid or reagents are introduced into wash port 104 and travels down wash fluid hole 186 to wash groove 210 in eleventh layer 206 and up slot 212 to reservoir 216 located below the level of heads 218 of wash needles 188 disposed in ninth layer 202.

The manner in the preferred embodiment in which an equal volume of wash fluid is supplied to each of the wash needles 188 is by having an equal length of each of the wash holes and wash channels from the reservoir 216 to each of the wash needles 188. This equality in length is accomplished by compensating for the position of a specific test tube 96 in rack 94 by lengthening the channels through the various layers 200, 198, 196, 194 and 192 as can be seen from FIGS. 14A-10A.

Figure 14A:
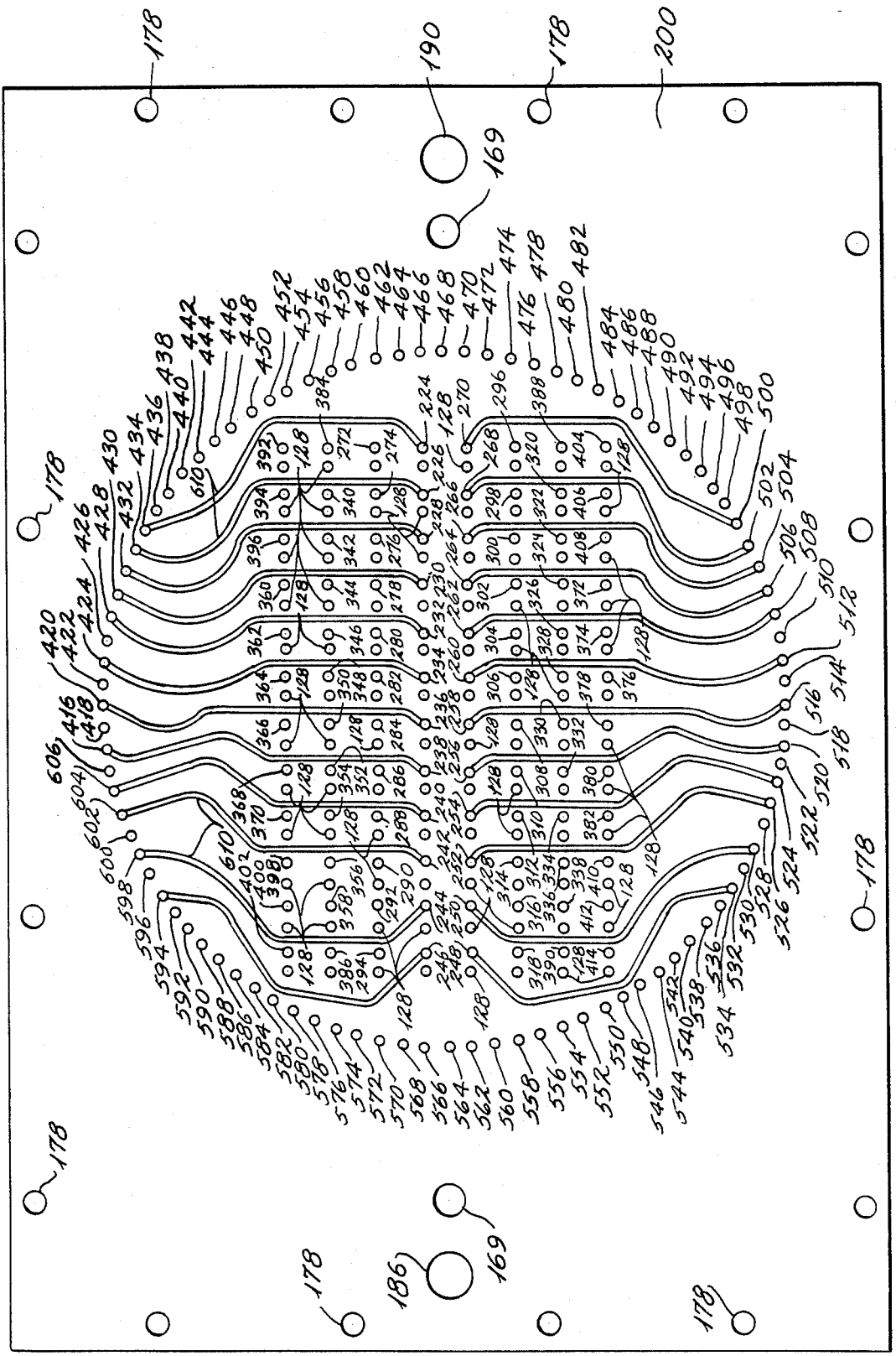
FIG. 14A is a top plan view of the eighth bottom layer of the multi-layered cell harvester.
Figure 14B:
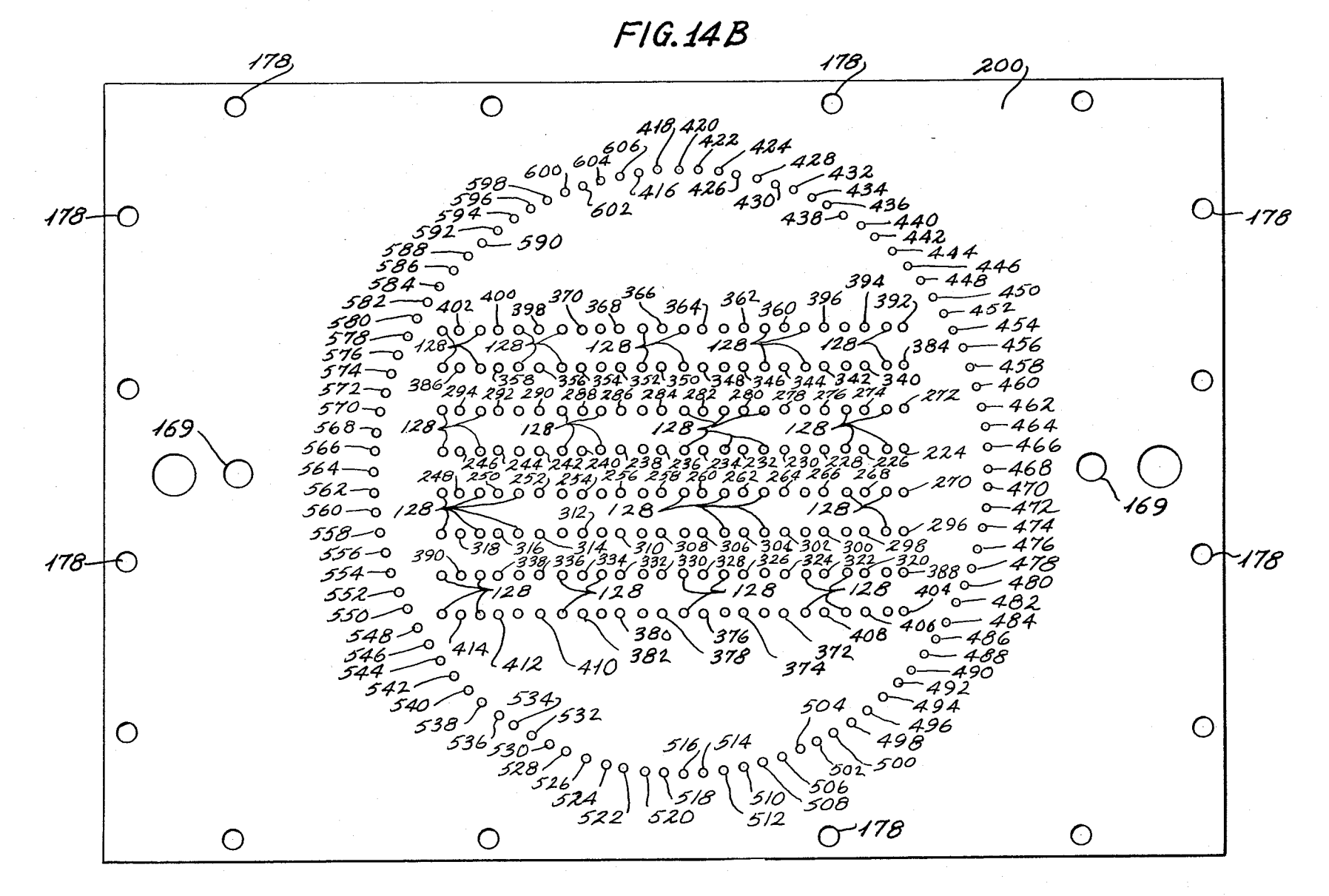
Figure 16A:
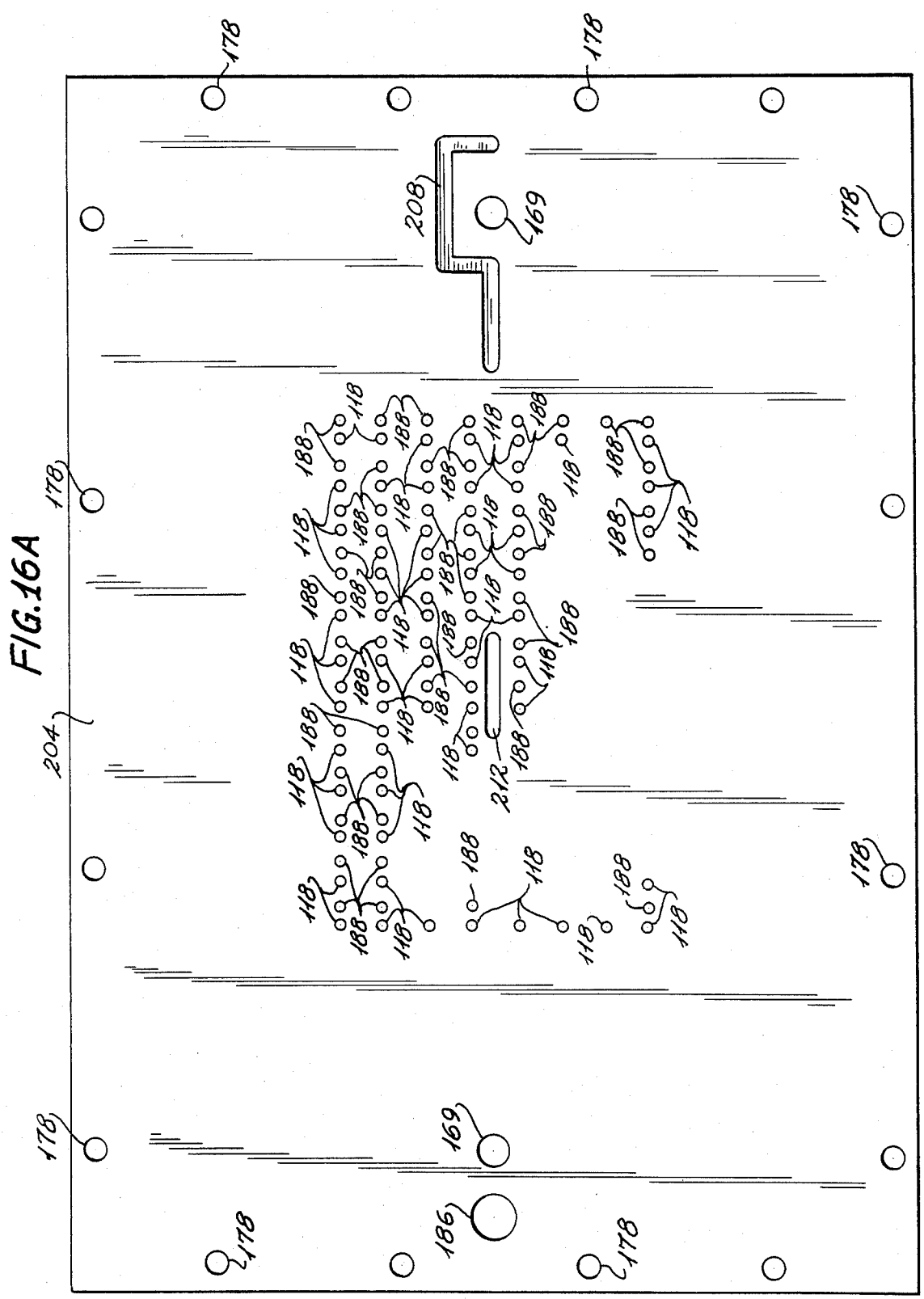
FIG. 16A is a top plan view of the top side of the tenth bottom layer of the multi-layered cell harvester.

As illustrated in FIG. 14A the combination of wash holes and wash channels providing wash fluid to wash needles located at the center of the array are longer than the combination of the length of the wash holes and wash channels for providing wash fluid to the wash needles located at the periphery of the array as illustrated in FIG. 10A. The combination of wash holes and wash channels have been calculated by computer to provide an equal length through the various layers and channels provided in the various layers to provide an equal volume of wash fluid or reagent to each of the test tubes 96 irrespective of their position in rack 94.

In the preferred embodiment the heads 218 of the wash needles 224-414 are disposed along side the head 219 of an evacuation needles 118 in the ninth layer 202. The paired arrangement of wash needles 224-414 and evacuation needles 118 are provided for their placement in the ¼ inch (6 mm) opening of each test tube 96. An O-ring 222 is provided for surrounding each of the heads 219 of the evacuation needles 118 and the heads 218 of the wash needles 224-414. Ninth layer 202 includes an opening 220 for receiving the respective head of the wash needles and evacuation needles and O-rings 222 for sealing the heads of the evacuation needles 118 and wash needles 224-414 up against eighth layer 200.

The evacuation needles 118 communicate with each of the 96 test tubes through evacuation holes 128 to each circular filter area surrounded by circular recess 160 and O-ring seal 162 (FIG. 7A). The combination of the evacuation holes 128 and the wash channels, wash holes and corresponding wash needles 224-414 provide for the removal, filtering and washing each of the test tubes and samples from the test tube array. The equal length of the wash holes and wash channels are important to provide an equal volume of wash fluid or reagent to each of the test tubes 96.

The equal length of the distance from each of the wash holes 416-604 to the tip of each of the wash needles 224-414 is maintained by varying the length or diameter of each of the wash holes or channels. This feature in combination with the design of reservoir 216 provides for the even displacement of air through the wash needles 224-414 and then the even distribution of fluid through the 96 holes 416-606 which connect reservoir 216 to each of the wash needles 224-414. The wash fluid is then evenly distributed through holes 416-606 through ninth layer 202 to eighth layer 200. At eighth layer 200 (FIG. 14A), the wash fluid exits various channels 610 to holes that connect each of the wash needles 224-270 with a corresponding test tube 96 in rack 94. It will be recognized that each of the channels 610 are of different composite length to make certain that each of the test tubes in the center of rack 94 receive the exact same amount of wash fluid or reagent to prevent any of the test tubes 96 from receiving more fluid at the expense of another or from over flowing from the introduction of wash fluid. Wash fluid flows through channels 610 to and then down through the wash holes in eighth layer 200 down to the corresponding wash needle in ninth level 202.

Wash fluid that does not flow through channels 610 to the inside rows of wash needles 188 continues to rise up through the remaining wash holes to the seventh layer 198 to be dispersed through channels 612 in the seventh layer 198. This wash fluid is distributed to wash needles 272 to 318 through corresponding numbered holes in the seventh layer after travelling down through layers 198 and 200 to the ninth layer 202. The channels 612 in seventh layer 198 are also of unequal length to uniformly supply water to each of the test tubes in the third and sixth rows in the 96 test tubes in rack 94. Wash fluid that has not exited channels 610 in the eighth layer 200 or channels 612 in the seventh layer 198 continues upward into sixth layer 196 to provide an even distribution to corresponding holes in the sixth layer to wash needles 320–358 through channels 614 in the sixth layer 196. The wash fluid flows through channels 614 into the corresponding wash holes in layer 196, seventh layer 198, eighth layer 200 and into the corresponding wash needles in ninth layer 200 for even distribution to the test tubes located in the second and seventh rows of the 96 test tube array in rack 94.

As can be seen, the channels 614 are similarly of uneven length to provide equal volume distribution of wash fluid to the test tubes in the second and seventh rows of rack 94. The length of the channels 614 in combination with the thickness of the layers 196–202 assures the even distribution of wash fluid to all of the test tubes in rows two and seven. Meanwhile the length of the channels 614 in combination with the thickness of layers 200–202 provides an even distribution of wash fluid to the test tubes in rows 4 and 5 of the test tubes 96. Similarly the length of channels 614 in combination with the thickness of layers 198–202 assures an even distribution of wash fluid to rows 3 and 6.

Figure 11B:
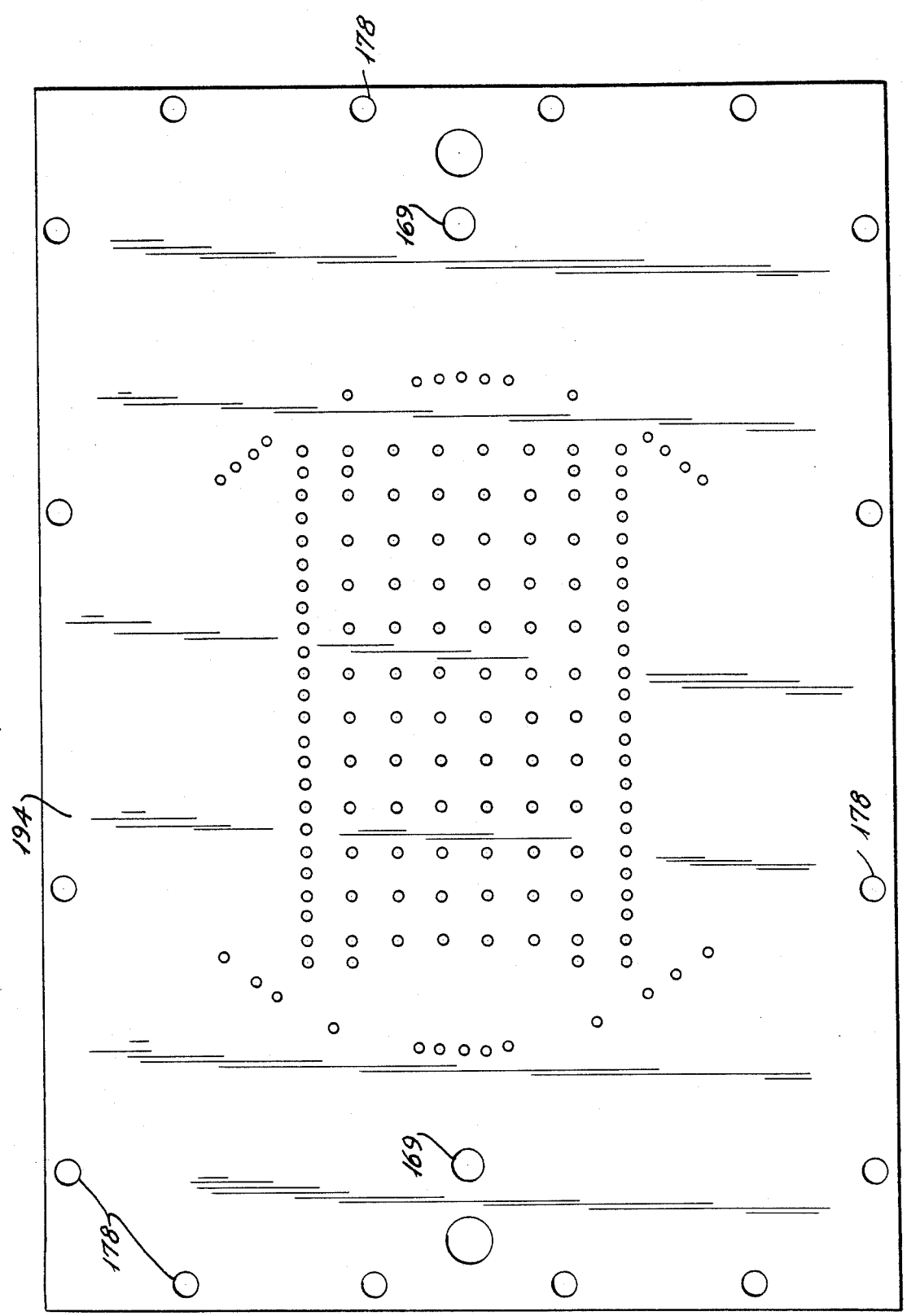
FIG. 11B is a plan view of the bottom of the fifth bottom layer of FIG. 11A of the multi-layered cell harvester.
Figure 13B:
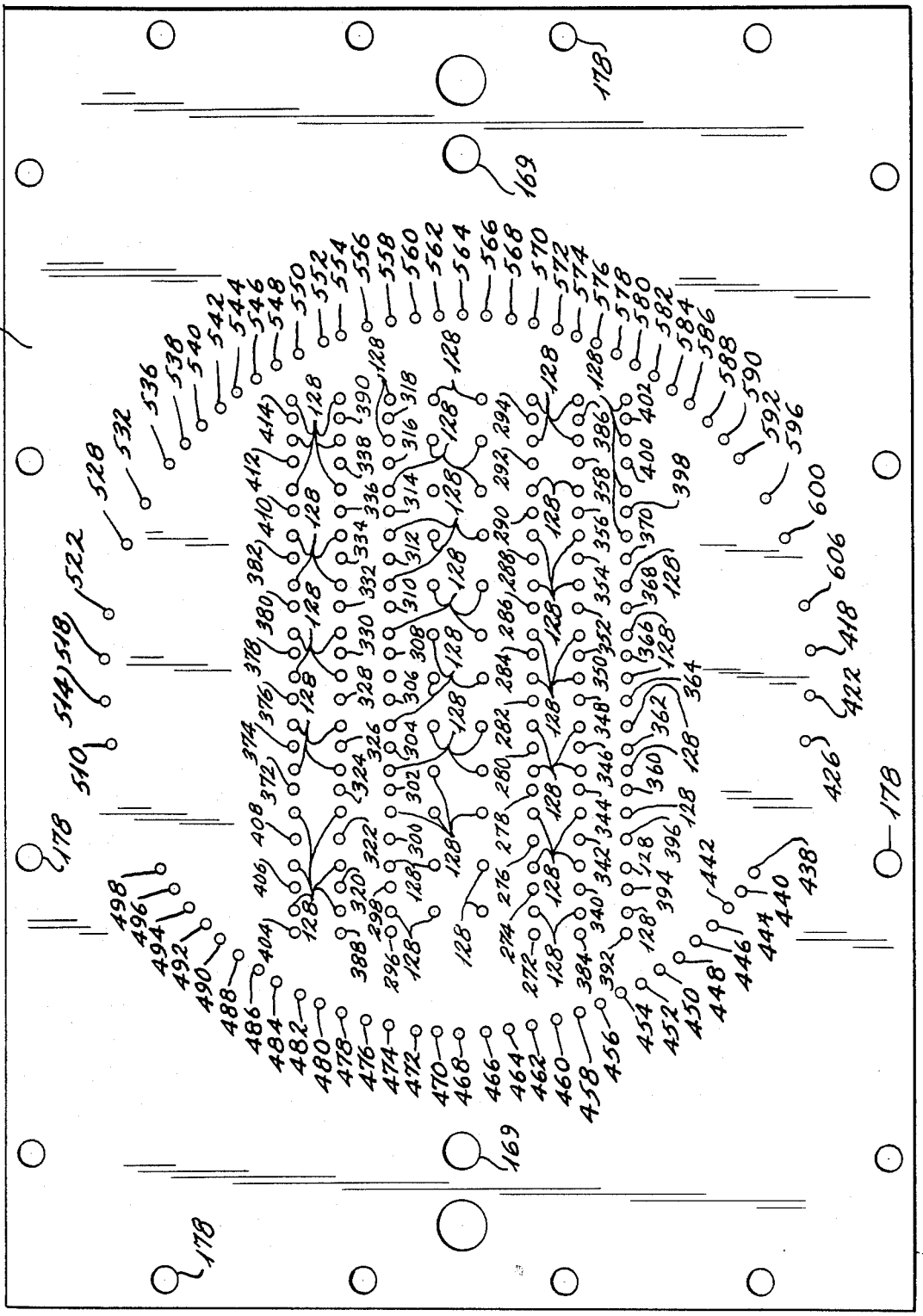
FIG. 13B is a plan view from the bottom side of FIG. 13A of the multi-layered cell harvester.

Wash fluid that has not exited channels 610, 612 or 614 Continues up through fifth layer 194 and enters channels 616 for even distribution down through layers 194, 196, 198, 200 and into the correspondingly numbered holes to corresponding needles 360–382 for even distribution to wash needles for some of the test tubes in the first and eighth rows. As can be seen the channels 616 in FIG. 11A are not of even length which in combination with the thickness of the layers 194–202 provides an even distribution of wash fluid to the corresponding test tubes in rows 1 and 8 of the test tubes 96. Wash fluid that has not exited channels 610, 612, 614 or 616 rises up through fourth layer 192 for distribution through channels 618 in fourth layer 192 to needles 384–414 through layers 192, 194, 196, 198 and 200 to the wash needles in the ninth layer 202.

The channels 618 are of unequal length and are designed to provide an even distribution of wash fluid to the remaining wash needles in the first, second, seventh and, eight rows of test tubes 96 in rack 94. As a result of the uneven length of the channels 610, 612, 614, 616 and 618 an even distribution of fluid to all of the wash needles is achieved through the utilization of the channels and the reservoir 216 having a cone shaped top add leveling means to assist in the even distribution of air and wash fluids or reagents. This assures that all of the test tubes 96 receive the exact same volume of fluid during a washing or reagent addition operation so that none of the test tubes 96 overflows or receives a greater amount of fluid at the expense of other wash needles 188.

As has been discussed the cone shaped reservoir 216 assists in the even distribution of wash fluid to all of the needles in the array. The vacuum port 100 activated by solenoid, similarly is utilized to prevent water from dripping from the wash needles 188 by evacuating reservoir 216 in a manner as has heretofore been described.

The vacuum applied to vacuum port 100 communicates via vacuum hole 190 to groove 208 to evacuate reservoir 216 and prevent water from the reservoir leaking back to the wash needles or otherwise interfering with the precise metering of wash fluid or reagents and the robotic operation for which the present invention is amenable.

As heretofore discussed, the novel multi-layer cell harvester 40 reduces the amount of time and work involved in removing samples from an array of small test tubes while filtering the contents of test tubes on ½ inch diameter (1.3 cm) filter areas on a sheet of filter paper. The advantages of the present invention can further be enhanced by the utilization of solenoids and various sensors or timers to automate and expedite the cell harvesting operation. For example, a roll of filter paper 620 (FIG. 3) can be attached and a motor utilized for the automatic feeding filter paper onto the filter paper support layer 50. When the filter paper is positioned in place, a motor is activated for pivoting and positioning the multiple top layers 42 in position with respect to the plurality of lower layers 48. The positioning of the top layers 42 activates a vacuum source to evacuate vacuum port 102, thereby clamping the multiple top layers 42 against the plurality of lower layers 48.

The clamping operation can then be utilized to activate a motor to raise test tube platform 84 into position in respect to the evacuation and wash needles 98 (FIG. 1). Once this operation is completed a vacuum can be activated from either primary vacuum connection housing 72 or secondary vacuum connection housing 78 to remove the contents of the individual test tubes 96 through evacuation needles 118. Once this operation has been completed, a further solenoid can be activated to introduce wash fluid to wash port 104 and into reservoir 216 for subsequent distribution to the plurality of wash needles 188 to provide a uniform distribution of wash fluid to all of the 96 test tubes in the array of test tubes 96 in rack 94.

Once wash fluid has been introduced a further removal of the wash water from each of the 96 test tubes can be accomplished by again activating the vacuum to either the primary vacuum connection housing 72 or the secondary vacuum connection housing 78, depending upon the type of wash and reagents that have been used. At that point a vacuum can be applied to vacuum port 100 to evacuate reservoir 216 in a manner as has been described, preventing any wash fluid from dripping through wash needles 188 into a new rack of test tubes that are subsequently placed in the novel cell harvester 40 for processing. A solenoid is activated at about the same time to release the vacuum from vacuum port 102 to allow the manual or robotic separation of the multiple top layers 42 from the plurality of lower layers 48. Thereafter a further motor can be activated to advance the filter paper 158 from the roll 620 to place a new section of filter paper in the novel cell harvester 40. The entire process can then be repeated. In addition, optional rolls or sheets of filter paper cell markers or identifiers along with counters and data markers can be installed to record each of the samples and information as to run date and time.

FIG. 18 is an exaggerated schematic presentation of a multi-layered cell harvester of the invention illustrating an arrangement of wash reservoir, wash water inlet and reservoir evacuation vacuum. In FIG. 18 the vacuum source for filtering and evacuating samples from the test tubes 96 utilizing evacuation needles 118 is illustrated in relation to the upper block and filter paper 158. The schematic drawing also shows the relationship, in exaggerated detail, between one of the wash needles 188 having a shorter wash or reagent channel and used for evacuating fluid in the middle rows of the test tubes 96 and a second evacuation needle 188A having a longer wash or reagent channel. The second evacuation needle 188A is used for washing a test tube 96 in the corner of one of the first or eighth rows. These rows require a longer length between the tip of the needle 188A and the reservoir 216. As heretofore discussed this arrangement provides an equal distribution of wash fluid to all of the test tubes 96 in the rack 94 irrespective of the position of the test tube in the rack 94.

As heretofore discussed, the invention may be implemented by changing the length of the channels from the reservoir 216 to the test tubes, by increasing the diameter of some of the channels to the test tubes, or by a combination of both. By one or a combination of these means, the invention provides an equal volume of wash fluid to all 96 test tubes in the rack 94 irrespective of their position in the rack 94. In this manner the invention provides for the precise metering of reagents or wash fluids to each of the test tubes.

As will be readily apparent to those skilled in the art, the novel multi-layered cell harvester 40 reduces the number of operational steps required to remove samples containing cells from a 96 standard test tube array as well as other numbers and sizes of test tubes while filtering and washing the test tubes on a full ½ inch (1.3 cm) area of filter paper. The invention is particularly applicable to small test tubes and small or critical volumes of materials as are currently utilized in the laboratory for cell harvesting studies. The novel cell harvester maintains a segregation of the filtered samples and liquid from each test tube and is susceptible to automated operation and can be utilized for radioactive or standard samples interchangeably. The novel cell harvester further can be modified to save the wash and mother liquid solutions by modifying the top layers of the multi-layered cell harvester.

The novel cell harvester of the present invention is amenable to robotic operation as a consequence of its design and precise metering and control of wash fluids. The advantages of the invention are further enhanced by the utilization of internal channels and the elimination of many of the hoses that would otherwise be required. The present invention therefore has a wide range of applicability and is susceptible to many modifications by those skilled in the art.

Figure 19:
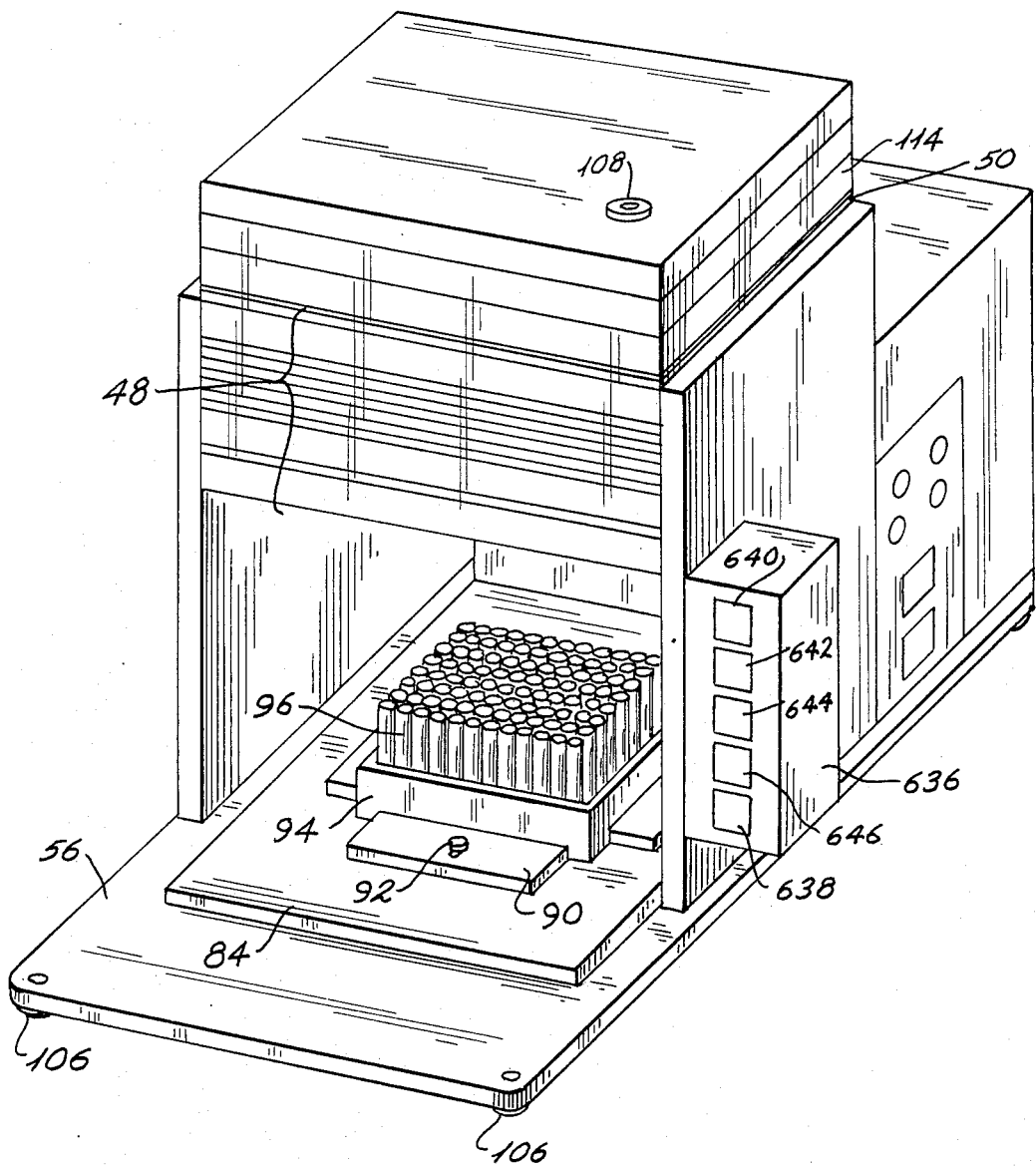
FIG. 19 is a perspective view of a further embodiment having a hinged top section and control section of a multi-layered cell harvester constructed in accordance with the present invention.
Figure 20:
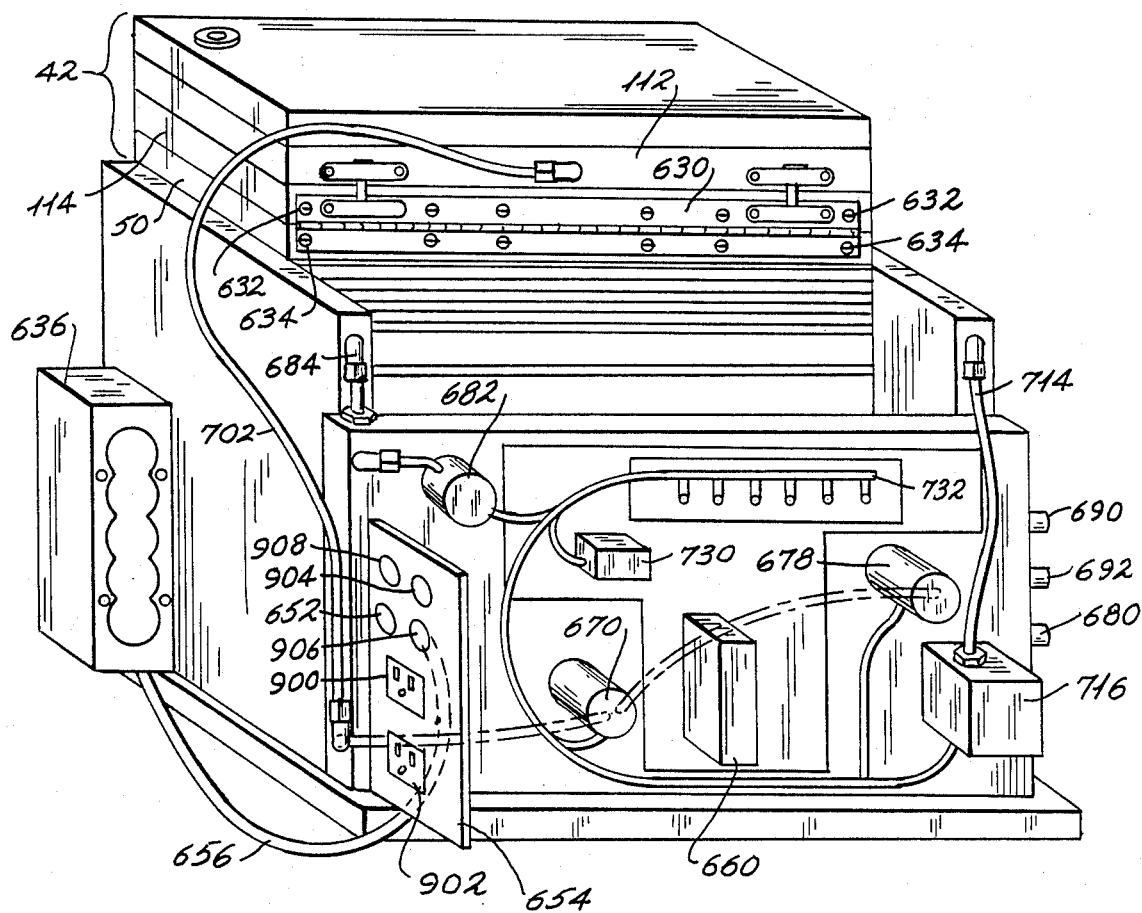
FIG. 20 is a rear elevational view of the multi-layered cell harvester of FIG. 19.
Figure 21:
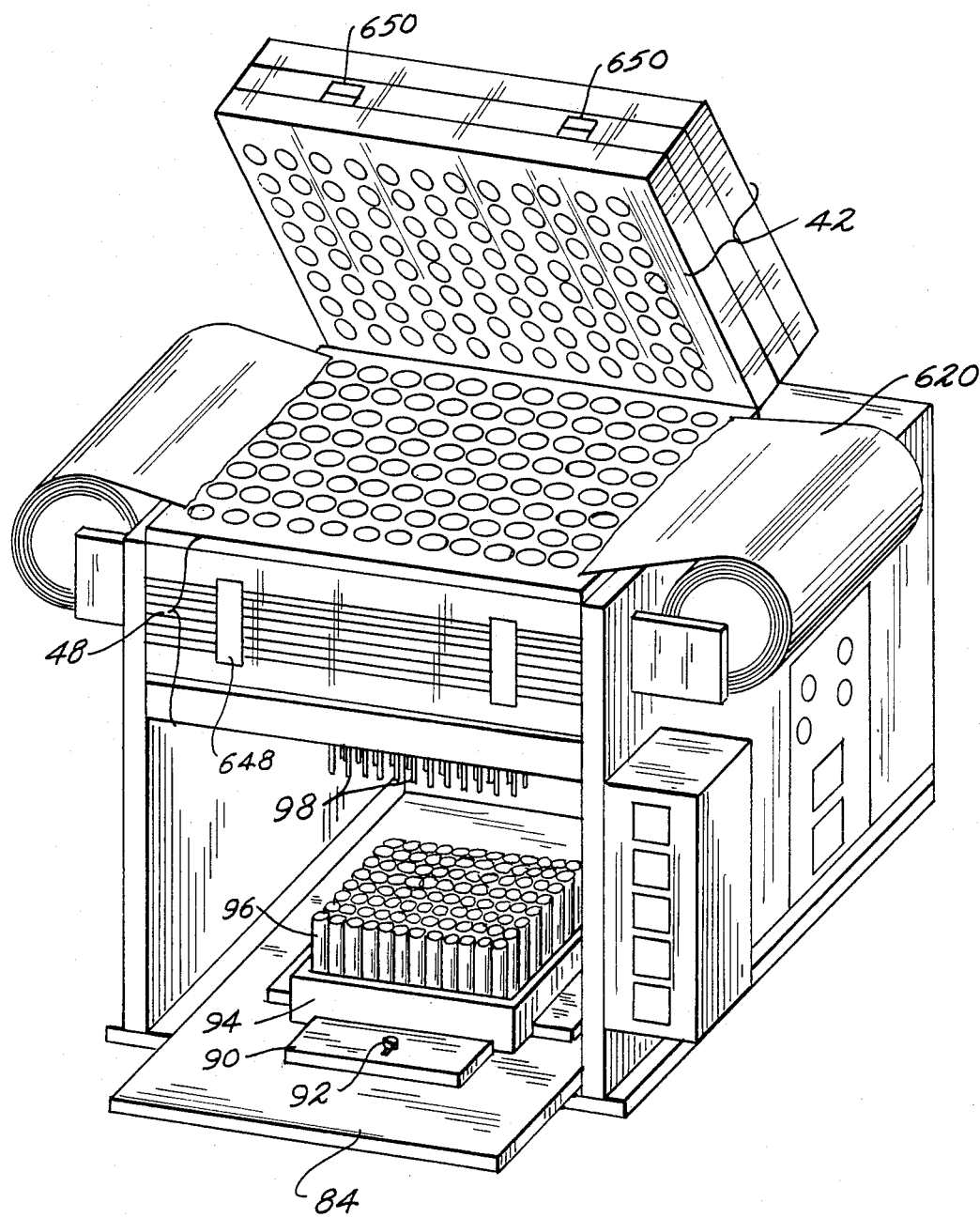
FIG. 21 is a perspective view of a multi-layered cell harvester similar to the multi-layered cell harvester of FIG. 19 including an automatic filter paper feed system.
Figure 22:
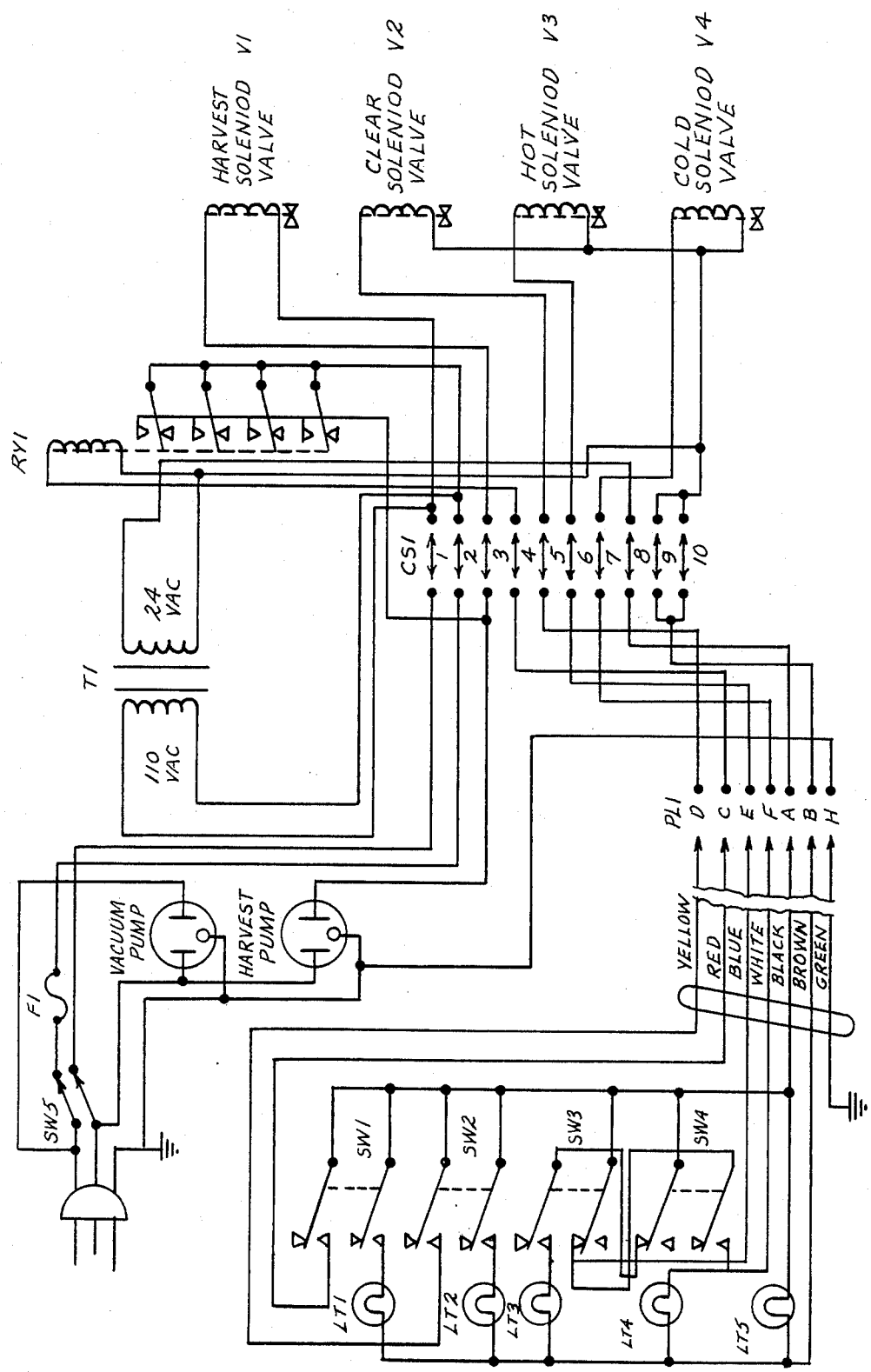
FIG. 22 is a circuit diagram of the circuitry of the cell harvester of FIG. 21.

Referring to FIGS. 19 and 20, a further embodiment of the multi-layered cell harvester having multiple top layers 42 and a plurality of lower layers is illustrated in which the multiple upper layers 42 are hinged to the plurality of lower layers 48. The multi-layered cell harvester includes a hinge 630 fastened on one side via screws 632 to the bottom top layer 114 while the other side of the hinge 630 is attached to the filter paper support layer 50 by screws 634. The multiple top layers 42 are similar in design and construction to the embodiment heretofore discussed except that it swings backward on hinge 630 as shown in FIG. 21. A roll of filter paper 620 may be added for the automated operation of the cell harvester.

The cell harvester as shown in FIGS. 19, 20, 21 and 23 include a control box 636 having a power ON light 638, a combined harvest light and switch 640 to turn the cell harveste ON and a clear manifold combined light and switch 642 for clearing reservoir 216 and wash needles 188. The cell harvester of FIGS. 19, 20 and 21 further inclucds a combined cold waste light and switch 644 for activating a vacuum source to withdraw the contents of the test tubes through the evacuation needles to the manifold in the multiple top layers 42. A hot or radioactive waste light switch and button 646 is provided for activating a optional secondary vacuum source for removing and disposing of radioactive fluids and reagents separately.

Referring now to FIGS. 19, 20, 21 and 22 the circuitry and control system will be described in greater detail. In the preferred embodiment a low voltage control box 636 is provided on the front side of the cell harvester in proximity to the operator while the high voltage circuitry is disposed away from the operator at the back of the cell harvester (FIG. 20). A cable 656 connects the low voltage control box to a panel 654 having a suitable power plug connection 652. Panel 654 includes an optional wash pump outlet 900 to connect and provide high voltage power to a conventional wash pump and an optional vacuum outlet 902 for connecting and supplying high voltage power to a vacuum pump. The novel cell harvester can utilize a separate vacuum pump or a vacuum source provided in the laboratory. A main power switch 908 and a fuse 904 can also be provided in panel 654.

Panel 654 is connected to a transformer 660 a relay 730 and a terminal strip 732 for supplying power to a clear manifold solenoid 682, a cold waste solenoid 670, a hot waste solenoid 678 and a wash fluid in solenoid 716. Solenoids 682, 670, 678 and 716 are operatively connected to control box 636 and the various vacuum and wash ports for supplying or withdrawing fluids from the cell harvester. More particularly, cold waste solenoid 670 and hot waste solenoid 678 are operatively connected to a cold waste/hot waste tube for withdrawing fluids from the manifold in multiple top layers 42.

Activation of power ON switch 908 turns ON power light 638 and cold waste switch 644 activates solenoid 670 to remove fluid from the test tubes 96 to the manifold in top layer 114 for discharge through cold waste and hot waste tube 702 to the manifold clear and cold waste port 692. Alternatively if switch 646 is activated, solenoid 678 activates the vacuum source to remove fluid from the test tubes 96 to the manifold in top layer 114 for discharge through cold waste hot waste tube 702 to the hot waste port 680 to provide for the separation of the radioactive materials from non radioactive materials.

The activation of switch 640 activates wash fluid solenoid 716 to cause a wash fluid or reagent pump to supply wash fluid or reagent to wash fluid in port 690 to supply wash fluid via wash fluid in tube 714 to the wash fluid reservoir located in the plurality of lower layers 48 and to each of the test tubes 96 in rack 94. After a precise and predetermined amount of wash fluid or reagent is added to the reservoir and test tubes the wash fluid or reagent pump is deactivated.

Thereafter, the activation of the clear manifold switch 642 activates solenoid 682 which is operatively connected to a clear manifold tube 684 that is connected to the vacuum manifold in the plurality of lower layers 48. The wash fluid or reagent is thus removed from the reservoir and the plurality of wash needles through the clear manifold tube 684 and out the manifold clear and cold waste port 692. As will be recognized by those skilled in the art, the invention can further be modified to add radioactive wash fluids or reagents by utilizing additional wash fluid or reagent, additional reservoirs or using the existing reservoir and discharging excess radioactive wash fluids or reagents through hot waste port 680 rather than through cold waste and manifold clear port 692.

The multiple top layers 42 are clamped to the plurality of lower layers by means of a clamp 648 (FIG. 21) disposed on the plurality of lower layers 48 with a corresponding catch 650 disposed on the multiple top layers 42. Once the multiple top layers 42 are manually clamped to the plurality of lower layers 48, the main power switch 908 is activated turning the power to the entire system on and where applicable the vacuum pump and the harvesting switch 640 is then activated turning on the power ON light 638 which is connected to a panel 654 via a cable 656 to activate a transformer 660 for regulating the supply of current and voltage to the solenoids and switches. The electronics for activating the various solenoids and relay can be of the type shown in FIG. 22 or may be standard electronic systems that may be readily assembled by those skilled in the art.

Figure 23:
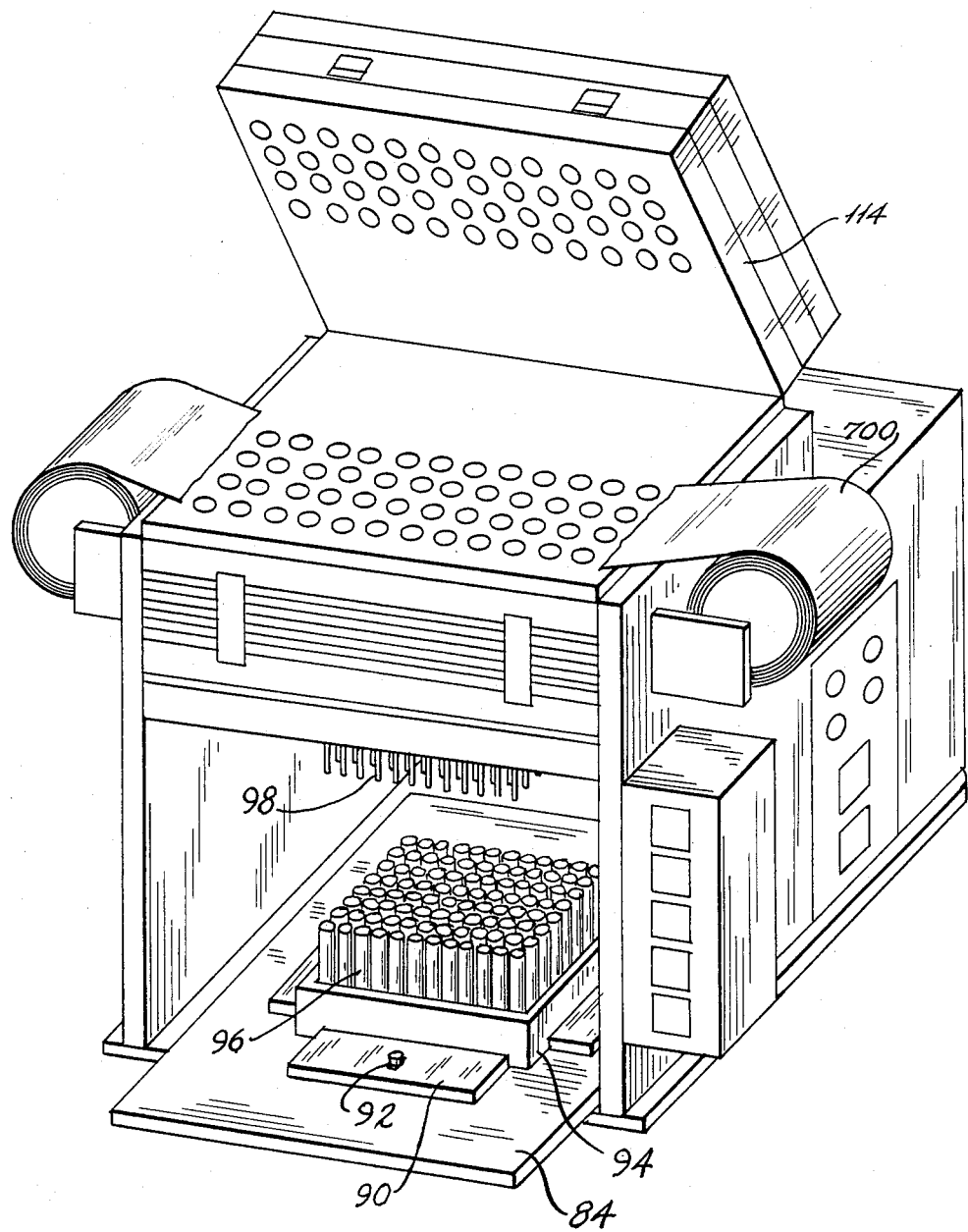
FIG. 23 is a perspective view of a multi-layered cell harvester similar to the multi-layered cell harvester of FIG. 21 designed for harvesting cells from 48 test tubes.

Referring now to FIG. 23, a multi-layered cell harvester for harvesting cells from small test tubes or from racks wherein the volume of reagents added to the test tubes must be critically controlled is illustrated utilizing 48 test tubes. The embodiment as illustrated in FIG. 23 is similar in operation and design as the previous multi-layered cell harvester and therefore a description of the components will not be repeated. However, in the embodiment as shown in FIG. 23 bottom top layer 114 and filter paper support layer include a provision for 48 samples instead of the 96 test tube array.

In the embodiment as shown in FIG. 23, the test tubes are of the same size as previously described and the distance between them are the same so that an increase in the spacing on the sheet of filter paper 700 is provided utilizing the expansion channels as previously described. The filter paper 700 is of a narrower format to filter the contents of each of the test tubes 96 onto a full ½ inch (1.3 cm) in diameter space on the filter paper 700. The embodiment as shown in FIG. 23 is similarly susceptible of robotic operation and control so as to expedite the filtering, sampling and washing operations of the cell harvester of the present invention.

Figure 24:
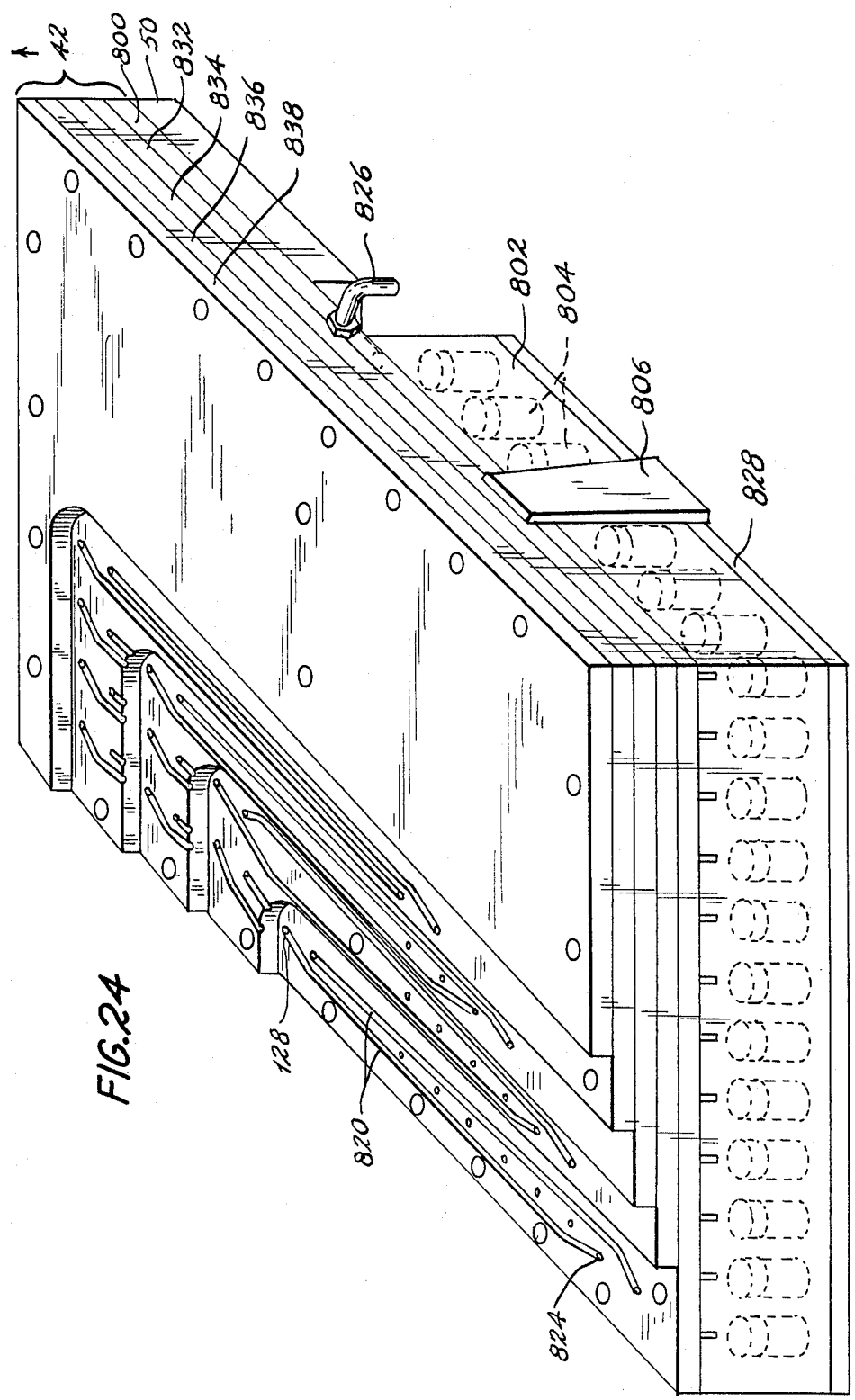
FIG. 24 is a perspective view partly in section of a modified top section of a multi-layered cell harvester having an arrangement for saving mother liquids or wash reagents.

Referring now to FIG. 24, a further embodiment of the invention is illustrated in which the multiple top layers 43 have been modified to provide a system for saving wash fluids or mother liquid from the 96 test tubes in rack 94. In FIG. 24 filter paper is placed between filter paper support layer 50 and bottom top layers 42 which are similar to the previous embodiments up to bottom top layer 114 and 112 except that layer 800 extends outward from the cell harvester to carry a tray 802 containing 96 sample collection vials 804 for saving the mother liquid or wash fluid from the 96 test tubes 96. The tray 802 is held in place up against layer 800 via clamps 806 or other suitable electro mechanical, mechanical or pneumatic means. The layer 800 also includes channels 820 which connect the evacuation holes 128 to holes 824 above the collection vials 804.

A vacuum source 826 is provided to supply vacuum to manifold 828 below sample vials 804 to draw fluid from the filter paper through the layer 800 through the channels 820 to corresponding holes disposed above the collection vials. Similarly, layers 832, 834, 836 and 838 are provided with channels leading to tray 802 for saving and separately discharging wash fluid or mother liquid from each of the test tubes 96 in rack 94.

The present invention has a wide range of applicability to cell harvester and filtering systems where the precise metering of fluids in small volumes to test tubes is desired, particularly in an automated or robotic type of operation. The invention may be implemented in a variety of ways by modifying and changing the levels and layers to achieve additional advantages such as the saving of the mother liquid, the filtrate and the wash water for both radioactive and non radioactive applications. The utilization of various vacuum sources for the segregation of each of the fluids from the 96 test tubes alone or in combination with the utilization of separate vacuum sources for radioactive and standard laboratory chemicals provide features that are environmentally advantageous in laboratory operations. In addition, the applicability of the present cell harvester for disassembly and sterilization by chemical and radioactive procedures or autoclaving of the various layers where the layers are made of metal or glass further provides advantages in analyzing and testing hazardous materials.

It will be further appreciated the present invention may be implemented in a variety of ways to suit the particular applications of the cell harvester by utilizing channels of varying length or varying size or combination thereof to provide a uniform and precise metering of wash fluid to various test tube samples. Consequently, it is intended that these and other modifications and applications of the invention to a variety of operations may be made within the spirit and scope of the invention as defined in the following claims.

What is claimed is:

1. A multi layered cell harvester for removing, filtering and adding precise quantities of wash fluids or reagents comprising:
  (a) a multi layered bottom section having a filter paper support layer;
  (b) a multi layered top section having a manifold and means for positioning said multi layered top section with respect to said multi layered bottom section;
  (c) a plurality of sample removal needles disposed in between one of the layers of said multi layered bottom section;
  (d) a plurality of filtration channels disposed in said multi layered bottom section and in said multi layered top section connecting said plurality of sample removal needles with said manifold in said multi layered top section;
  (e) a plurality of wash or reagent addition needles disposed in between one of the layers of said multi layered bottom section;
  (f) a wash or reagent reservoir disposed in between one of the layers of said multi layered bottom section; and
  (g) a plurality of wash or reagent addition channels connecting said reservoir with said plurality of wash or reagent needles and providing a substantially equal volume distribution of wash fluid or reagent to a plurality of test tubes by equalizing the length of each of said plurality of wash or reagent addition channels from the tip of each wash or reagent addition needle to said reservoir or by increasing the diameter of one or more of said wash or reagent addition channels or a combination thereof.

2. The multi layered cell harvester of claim 1 wherein said multi layered bottom section includes said plurality of filtration channels spread apart.

3. The multi layered cell harvester of claim 1 wherein said wash or reagent reservoir includes a conical shaped projection disposed from the top of said reservoir.

4. The multi layered cell harvester of claim 3 further comprising a vacuum manifold disposed in between one of the layers of said multi layered bottom section operatively connected to said wash or reagent reservoir.

5. The multi layered cell harvester of claim 3 or 4 further comprising a means for leveling the multi layered cell harvester.

6. The multi layered cell harvester of claim 1 wherein said manifold in said multi layered top section includes means for preventing fluid from re-entering said plurality of filtration channels.

7. The multi layered cell harvester of claim 6 wherein said means for preventing fluid from re-entering said plurality of filtration channels comprises a termination of said filtration channels at a level higher than the bottom plane of said manifold in said multi layered top section.

8. The multi layered cell harvester of claim 1 wherein the tip of said sample removal needles and the tip of said wash or reagent addition needles are tapered toward each other.

9. The multi layered cell harvester of claim 1 wherein said plurality of sample removal needles and said plurality of wash or reagent addition needles are disposed in between the same layers of said multi layered bottom section.

10. The multi layered cell harvester of claim 9 wherein said wash or reagent reservoir is disposed in between one of the layers located below the layer of said plurality of sample removal needles and said plurality of wash or reagent addition needles in said multi layered bottom section.

11. The multi layered cell harvester of claim 1 wherein said manifold in said top section includes a first vacuum port for non-radioactive materials and a second vacuum port for radioactive materials.

12. The multi layered cell harvester of claim 1 wherein said means for positioning said multi layered top section with respect to said multi layered bottom section includes a pivotal mounting of said multi layered top section with respect to said multi layered bottom section.

13. The multi layered cell harvester of claim 1 or claim 12 further comprising means for automatically feeding filter paper to said filter paper support layer of said multi layered bottom section.

14. The multi layered cell harvester of claim 1 or 12 further comprising a vacuum manifold disposed in between one of the layers of said multi layered bottom section for clamping said multi layered top section with respect to said multi layered bottom section.

15. The multi layered cell harvester of claim 1 wherein said multi layered top section includes means for saving the mother liquid or wash reagents removed from said test tubes by said plurality of said sample removal needles.

16. The multi layered cell harvester of claim 14 wherein said means for saving the mother liquid or wash reagents further comprising a detachable tray disposed between plurality of filtration channels and said manifold in said multi layered top section.

17. A multi layered laboratory apparatus for filtering and adding precise quantities of wash fluids or reagents comprising:
(a) a multi layered bottom section;
(b) a multi layered top section pivotally mounted with respect to said multi layered bottom section, said multi layered top section including a manifold;
(c) a plurality of sample removal needles disposed in said multi layered bottom section;
(d) a plurality of filtration channels connecting said plurality of sample removal needles with said multi layered top section;
(e) a plurality of wash or reagent addition needles disposed in said multi layered bottom section; and
(f) a plurality of wash fluid or reagent addition channels connecting a wash fluid or reagent source with said plurality of sample removal needles and providing an equal volume distribution of wash fluid or reagent to an array of containers by having the length of each of said wash fluid or reagent addition channels of equal length or by increasing the diameter of some of said wash fluid or reagent addition channels or a combination thereof.

18. The multi layered laboratory apparatus of claim 17 further comprising a wash fluid or reagent source disposed between one or more of the layers of said multi layered bottom section.

19. The multi layered laboratory apparatus of claim 18 wherein said wash fluid or reagent source includes a conical shaped projection extending down from the top of said wash fluid or reagent source.

20. The multi layered laboratory apparatus of claim 18 further comprising a vacuum source for removing wash fluid or reagent from said wash fluid or vacuum source, said plurality of wash fluid or reagent addition channels and said plurality of sample removal needles.

21. The multi layered laboratory apparatus of claim 17 further comprising a means for automatically feeding sheets of filter paper between said multi layered bottom section and said multi layered top section.

22. The multi layered laboratory apparatus of claim 17 further comprising a vacuum manifold disposed between one of the layers of said multi layered bottom section for clamping said multi layered top section with respect to said multi layered bottom section.

23. The multi layered laboratory apparatus of claim 17 wherein said multi layered top section includes means for saving mother liquid or wash reagents removed from said array of containers by said plurality of sample removal needles.

24. A multi layered device for removing, filtering and adding precise quantities of fluids to an array of sample containers comprising:
(a) a multi layered bottom section having a filter paper support layer;
(b) a multi layered top section having a manifold and vacuum source;
(c) a plurality of sample removal needles disposed in one of the layers of said multi layered bottom section;
(d) a plurality of filtration channels connecting said plurality of sample removal needles with said manifold of said multi layered top section;
(e) a plurality of fluid addition needles disposed in one of the layers of said multi layered bottom section;
(f) a reservoir disposed in one of the layers of said multi layered bottom section said reservoir disposed in a layer located below said plurality of fluid addition needles;

(g) a plurality of fluid addition channels connecting said reservoir with said plurality of fluid addition needles and providing a substantially equal volume of fluid to an array of sample containers by providing a constant distance from said reservoir to the tip of each of said plurality of fluid addition needles where a constant diameter of said fluid addition channels is maintained or by varying the diameter of said fluid addition channels where said constant distance is not maintained or by varying both the diameter and the distance of said fluid addition channels; and (h) a vacuum manifold disposed in said multi layered bottom section for removing wash fluid or from said reservoir, said plurality of fluid addition channels and said plurality of fluid addition needles.

25. The multi layered device of claim 24 wherein said reservoir includes a conical shaped projection from the top of said reservoir.

26. The multi layered device of claim 24 or 25 further comprising a means for leveling the multi layered cell harvester.

27. The multi layered device of claim 24 wherein said manifold in said multi layered top section includes means for preventing fluid from re-entering said plurality of filtration channels.

28. The multi layered device of claim 27 wherein said means for preventing fluid from re-entering said plurality of filtration channels comprises the termination of said filtration channels at a level higher than the bottom of said manifold in said multi layered top section.

29. The multi layered device of claim 24 wherein the tip of said sample removal needles and the tip of said fluid addition needles are tapered toward each other.

30. The multi layered cell harvester of claim 24 wherein said manifold in said top section includes a first vacuum source for non-radioactive materials and a second vacuum source for radioactive materials.

31. The multi layered device of claim 24 further comprising a vacuum manifold disposed in one of the layers of said multi layered bottom section for clamping said multi layered top section with respect to said multi layered bottom section.

* * * * *